US012606798B2

(12) United States Patent
Slukvin et al.

(10) Patent No.: US 12,606,798 B2
(45) **Date of Patent: *Apr. 21, 2026**

(54) METHODS AND MATERIALS FOR HEMATOENDOTHELIAL DIFFERENTIATION OF HUMAN PLURIPOTENT STEM CELLS UNDER DEFINED CONDITIONS

(71) Applicant: WISCONSIN ALUMNI RESEARCH FOUNDATION, Madison, WI (US)

(72) Inventors: Igor Slukvin, Verona, WI (US); Gene Ichiro Uenishi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 636 days.

This patent is subject to a terminal disclaimer.

(21) Appl. No.: 17/715,889

(22) Filed: Apr. 7, 2022

(65) Prior Publication Data

US 2022/0228118 A1 Jul. 21, 2022

Related U.S. Application Data

(63) Continuation of application No. 15/917,504, filed on Mar. 9, 2018, now abandoned, which is a continuation of application No. 14/206,778, filed on Mar. 12, 2014, now Pat. No. 9,938,499.

(60) Provisional application No. 61/779,564, filed on Mar. 13, 2013.

(51) Int. Cl.
| *C12N 5/00* | (2006.01) |
| *C12N 5/071* | (2010.01) |
| *C12N 5/0783* | (2010.01) |
| *C12N 5/0789* | (2010.01) |
| *C12N 5/095* | (2010.01) |

(52) U.S. Cl.
CPC ......... *C12N 5/0647* (2013.01); *C12N 5/0056* (2013.01); *C12N 5/0636* (2013.01); *C12N 5/069* (2013.01); *C12N 5/0695* (2013.01); *C12N 2500/02* (2013.01); *C12N 2501/115* (2013.01); *C12N 2501/155* (2013.01); *C12N 2501/16* (2013.01); *C12N 2501/165* (2013.01); *C12N 2502/1394* (2013.01); *C12N 2506/02* (2013.01); *C12N 2506/45* (2013.01); *C12N 2533/54* (2013.01)

(58) Field of Classification Search
CPC ............................... C12N 5/0056; C12N 5/00
See application file for complete search history.

(56) References Cited

U.S. PATENT DOCUMENTS

| 7,615,374 | B2 | 11/2009 | Vodyanyk et al. |
| 7,811,821 | B2 | 10/2010 | Slukvin et al. |
| 8,034,613 | B2 | 10/2011 | Slukvin et al. |
| 8,133,732 | B2 | 3/2012 | Slukvin et al. |
| 8,158,422 | B2 | 4/2012 | Slukvin et al. |
| 8,183,038 | B2 | 5/2012 | Thomson et al. |
| 8,372,642 | B2 | 2/2013 | Rajesh et al. |
| 8,372,643 | B2 | 2/2013 | Ying et al. |
| 8,435,785 | B2 | 5/2013 | Slukvin et al. |
| 8,440,461 | B2 | 5/2013 | Thomson et al. |
| 2008/0070303 | A1 | 3/2008 | West et al. |
| 2010/0261274 | A1 | 10/2010 | Vodyanyk et al. |

FOREIGN PATENT DOCUMENTS

| AU | 2007215276 B2 | 8/2007 |
| AU | 2008231020 B2 | 10/2008 |
| GB | 2440494 B2 | 7/2010 |
| GB | 2449042 B | 7/2010 |
| IL | 187628 A | 5/2012 |
| IL | 200982 A | 3/2013 |
| SE | 702695 A | 12/2007 |
| SG | 137991 | 3/2011 |
| WO | 2009137629 A2 | 11/2009 |
| WO | 2010099539 A1 | 9/2010 |
| WO | 2010143529 A1 | 12/2010 |
| WO | 2011139628 A1 | 11/2011 |
| WO | 2014165131 A1 | 10/2014 |

OTHER PUBLICATIONS

Furukawa et al. (2019, JSRM vol. 15, pp. 45-51) (Year: 2019).*
Chung et al. (2024, Biomedicines, vol. 12, pp. 1-22) (Year: 2024).*
Ameri, et al. FGF2 specifies hESC-derived definitive endoderm into Foregut/Midgut cell lineages in a concentration-dependent manner. Stem Cells, (2010), 28(1):45-56.
Ballard, et al. Vascular Tenascin-C Regulates Cardiac Endothelial Phenotype and Neovascularization. FASEB Journal, 2006, 20:717-719.
Bertho, et al. Reinjection of Ex Vivo-Expanded Primate Bone Marrow Mononuclear Cells Strongly Reduces Radiation-induced Aplasia. Journal of Hematotherapy & Stem Cell Research, 2002, 11: 549-564.
Bitmasour, et al. Single infusion of myeloid progenitors reduces death from Aspergillus fumigatus following chemotherapy-induced neutropenia. Blood. 2005, 105(9): 3535-3537.
Cerdan, et al. Activin A Promotes Hematopoietic Fated Mesoderm Development Through Upregulation of Brachyury In Human Embryonic Stem Cells. Stem Cells and Development, 2012, 21(15):2866-2877.
Chen, et al., Chemically Defined Conditions for Human iPS Cell Derivation and Culture. Nature Methods, 2011, 8(5):424-429.
Choi, et al. Identification of the Hemogenic Endothelial Progenitor and Its Direct Precursor in Human Pluripotent Stem Cell Differentiation Cultures. Cell Reports, 2012, 2(3):553-567.
D'Amour, et al., Efficient differentiation of human embryonic stem cells to definitive endoderm. Nature Biotechnology, 2005, 23(12):1534-1541.

(Continued)

*Primary Examiner* — Anoop K Singh
*Assistant Examiner* — David A Montanari
(74) *Attorney, Agent, or Firm* — McDonnell Boehnen Hulbert & Berghoff LLP

(57) ABSTRACT

Methods, kits and compositions for differentiating pluripotent stem cells into cells of endothelial and hematopoietic lineages are disclosed.

9 Claims, 10 Drawing Sheets
(5 of 10 Drawing Sheet(s) Filed in Color)

(56) References Cited

OTHER PUBLICATIONS

Eiselleova, et al. A complex role for FGF-2 in self-renewal, survival, and adhesion of human embryonic stem cells. Stem Cell, 2009, 27(8):1847-1857.

Ferrari, et al. IgG subclass distribution of anti-ADAMTS13 antibodies in patients with acquired thrombotic thrombocytopenia purpura. J. Thrombosis and Haemostasis, 2009, 7(10):1703-1710.

Jin et al. Erythropoietic potential of CD34+ Hematopoietic Stem Cells from human cord blood and G-CSF-mobilized peripheral blood. BioMed Res. Int., 2014, Article ID 435215, p. 1-9.

Kennedy, et al. T Lymphocyte Potential Marks the Emergence of Definitive Hematopoietic Progenitors in Human Pluripotent Stem Cell Differentiation Cultures. Cell Reports, 2012, 2:1722-1735.

Lonergan et al. Sickle Cell Anemia. RadioGraphics, 2001, 21(4)971-994.

Marshall, et al. Detailed Characterization of the Human Aorta-Gonad-Mesonephros Region Reveals Morphological Polarity Resembling a Hematopoietic Stromal Layer. Developmental Dynamics, 1999, 215:139-147.

Muntean et al. The pathogenesis of mixed-lineage leukemia. Annu. Rev. Pathol. Mech. Dis., 2012, 7:283-301.

Nakamura-Ishizu, et al. Extracellular Matrix Protein Tenascin-C is Required in the Bone Marrow Microenvironment Primed for Hematopoietic Regeneration. Blood, 2012, 119(23):5429-5437.

Niwa, et al. A Novel Serum-Free Monolayer Culture for Orderly Hematopoietic Differentiation of Human Pluripotent Cells Via Mesodermal Progenitors. PLoS One, 2011, 6(7):e22261 (11 pages).

Ohta, et al. Suppression of Hematopoietic Activity in Tenascin-C-Deficient Mice. Blood, 1998, 91(11):4074-4083.

Pearson, et al. The Stepwise Specification of Embryonic Stem Cells to Hematopoietic Fate is Driven by Sequential Exposure to Bmp4, Activin A, bFGF and VEGF. Development, 2008, 135:1525-1535.

Pick, et al. Differentiation of Human Embryonic Stem Cells in Serum-Free Medium Reveals Distinct Roles for Bone Morphogenetic Protein 4, Vascular Endothelial Growth Factor, Stem Cell Factor, and Fibroblast Growth Factor 2 InHematopoiesis. Stem Cells, 2007, 25:2206-2214.

Ramirez-Bergeron, et al. Hypoxia affects mesoderm and enhances hemangioblast specification during early development. Development 131.18 (2004): 4623-4634.

Sakurai, et al. Bidirectional induction toward paraxial mesodermal derivatives from mouse ES cells in chemically defined medium. Stem cell research 3.2-3 (2009): 157-169.

Salvagiotto, et al., A Defined, Feeder-Free, Serum-Free System to Generate In Vitro Hematopoietic Progenitors and Differentiated Blood Cells from hESCs and hiPSCs. PLoS One, 2011, 6(3):e17829.

Seiffert, et al. Mitogenic and adhesive effects of tenascin-C on human hematopoietic cells are mediated by various functional domains. Matrix biology 17.1 (1998): 47-63.

Seki, et al., Identification of Tenascin-C as a Key Molecule Determining Stromal Cell-Dependent Erythropoiesis. Experimental Hematology, 2006, 34(4):519-527.

Singh, et al., Myeloid Progenitors: A Radiation Countermeasure that is Effective when Initiated Days after Irradiation. Radiation Research. 2012, 177: 781-791.

Slukvin, Deciphering the Hierarchy of Angiohematopoietic Progenitors from Human Pluripotent Stem Cells. Cell Cycle, 2013, 12(5):720-727.

Smith, et al., The Aryl Hydrocarbon Receptor Directs Hematopoietic Progenitor Cell Expansion and Differentiation. Blood, 2013, 122(3):376-385.

Xu et al. BMP4 innitiates human embryonic stem cell differentiation to trophoblast. Nature Biotechnology, 2002, 20(12):1261-1264.

Valencia, et al., Transient B-catenin Stabilization Modifies Lineage Output from Human Thymic CD34+CD1a-Progenitors. Journal of Leukocyle Biology, 2010, 87(3):405-414.

Vodyanik, et al., Human Embryonic Stem Cell-Derived CD34+ Cells: Efficient Production in the Coculture with OP9 Stromal Cells and Analysis of Lymphohematopoietic Potential. Blood, 2005, 105(2):617-626.

Vodyanik, et al., Leukosialin (CD43) Defines Hematopoietic Progenitors in Human Embryonic Stem Cell Differentiation Cultures. Blood, 2006, 108(6):2095-2105.

Vodyanik, et al., A Mesoderm-Derived Precursor for Mesenchymal Stem and Endothelial Cells. Cell Stem Cell, 2010, 7(6):718-729.

Wang, et al., TGFbeta Inhibition Enhances the Generation of Hematopoietic Progenitors from Human ES Cell-Derived Hemogenic Endothelial Cells Using a Stepwise Strategy. Cell Research, 2012, 22:194-207.

Zimmerman, et al., Clinical impact of ex vivo differentiated myeloid precursors after high-dose chemotherapy andperipheral blood progenitor cell rescue. Bone Marrow Transplation. 2000, 26: 505-510.

PCT International Search Report and Written Opinion, PCT/US2014/024518, Jul. 24, 2014.

* cited by examiner

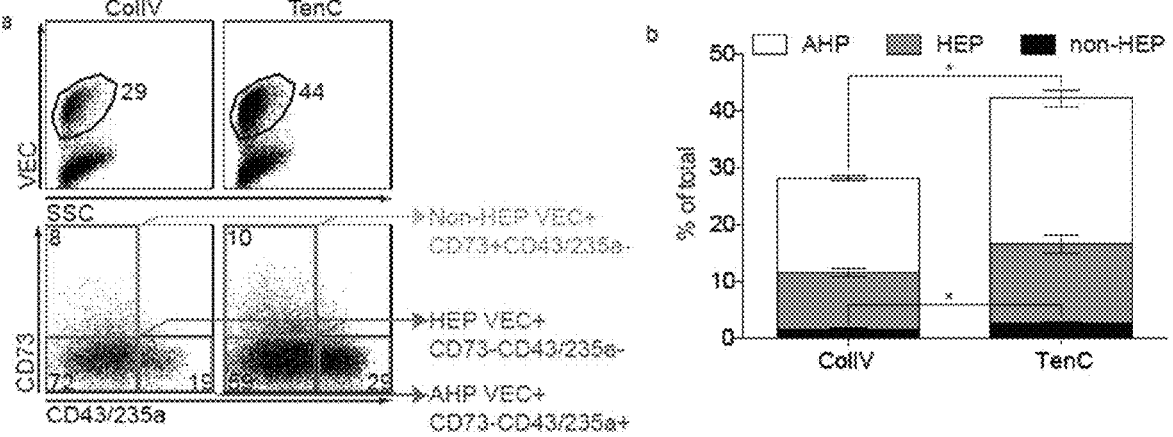
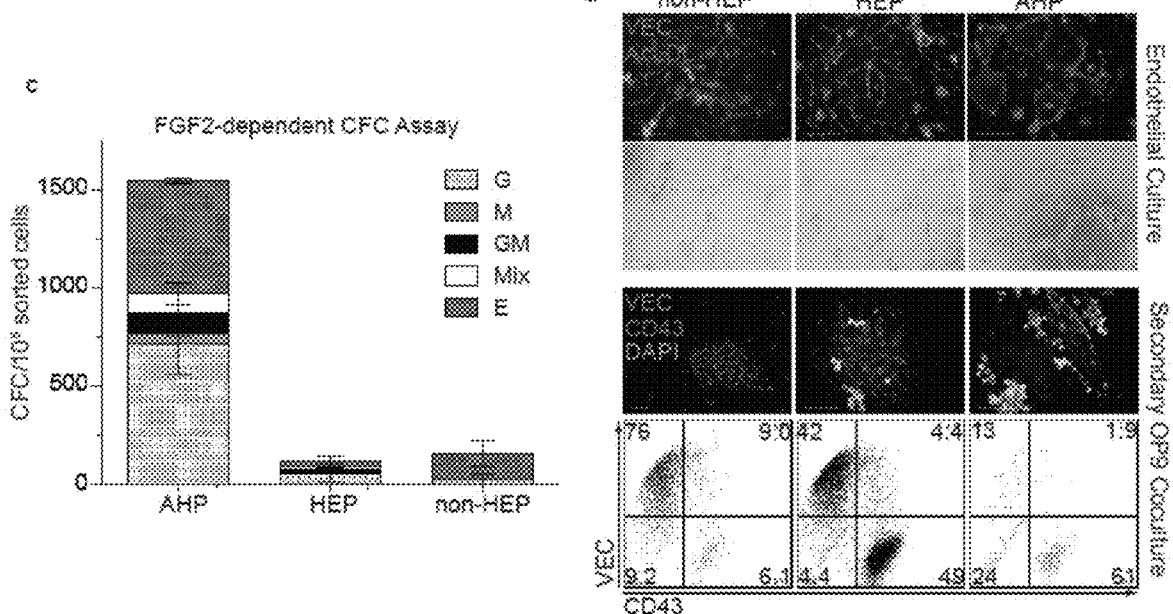
FIGS. 4A-4D

METHODS AND MATERIALS FOR HEMATOENDOTHELIAL DIFFERENTIATION OF HUMAN PLURIPOTENT STEM CELLS UNDER DEFINED CONDITIONS

CROSS-REFERENCE TO RELATED APPLICATIONS

This application is a continuation of U.S. patent application Ser. No. 15/917,504 filed on Mar. 9, 2018, which is a continuation of U.S. patent application Ser. No. 14/206,778, filed Mar. 12, 2014, now U.S. Pat. No. 9,938,499, granted Apr. 10, 2018, which claims the benefit of U.S. Provisional Application No. 61/779,564 filed on Mar. 13, 2013, the contents of which are incorporated by reference in their entireties.

STATEMENT REGARDING FEDERALLY SPONSORED RESEARCH/DEVELOPMENT

This invention was made with government support under Grants No. HL099773 and HL116221 awarded by the National Institutes of Health. The government has certain rights in the invention.

BACKGROUND OF THE INVENTION

The advent of human pluripotent stem cell technologies has provided the opportunity to produce endothelial and hematopoietic cells in vitro for functional studies and therapies. Previously, co-culture systems using the mouse bone marrow stromal cell line, OP9, have been used to establish efficient and scalable differentiation of human pluripotent stem cells (hPSCs) into endothelial and blood lineages. However, co-culture systems that rely on mouse feeder cells and serum (i.e., xenogenic sources) have limited utility for studying hPSC response to specific growth factors. Moreover, such systems have further limitations when considered in the context of manufacturing clinical grade therapeutic blood cells.

In light of the shortcomings of prior culture systems, new culture systems are needed to provide sources of endothelial and blood lineages that are suitable for use in clinical settings without the risk of introduction of xenogenic contamination.

SUMMARY OF THE INVENTION

In one aspect provided herein is a method for differentiating human pluripotent stem cells comprising: (a) providing human pluripotent stem cells; and (b) culturing the human pluripotent stem cells under hypoxic conditions in a cell culture medium comprising FGF2, BMP4, Activin A, and LiCl for a period of about two days to form a cell population of $^{EMH}$lin$^-$KDR$^+$APLNR$^+$PDGFRalpha$^+$ primitive mesoderm cells with mesenchymoangioblast potential.

In some embodiments the method also includes the step of (c) exposing cells at the primitive mesoderm stage of step (b) to a mixture comprising components FGF2 and VEGF under hypoxic conditions for a period of about 1-2 days to obtain a population comprising $^{EMH}$lin$^-$KDR$^+$APLNR$^+$PDGFRalpha$^+$ primitive mesoderm with hemangioblast (HB-CFC) potential and hematovascular mesoderm cells ($^{EMH}$lin$^-$KDR$^{hi}$APLNR$^+$PDGFRalpha$^{lo/-}$) with a potential to form hematoendothelial clusters when cultured on OP9 cells. In some embodiments, the method further includes the step of:

(d) exposing the cells at the hematovascular mesoderm stage of step (c) to a mixture comprising components FGF2, VEGF, IL6, SCF, TPO, and IL3 for about one day to achieve formation of CD144$^+$CD73$^+$CD235a/CD43$^-$ non-hemogenic endothelial progenitors (non-HEP), CD144$^+$CD73$^-$CD235a/CD43$^-$ hemogenic endothelial progenitors (HEPs), CD144$^+$CD73$^-$CD235a/CD43$^+$41a$^-$ angiogenic hematopoietic progenitors (AHP), and CD43$^+$CD41a$^+$ hematopoietic progenitor cells. In further embodiments, the method also comprises the step of: (e) continuing to expose the HEPs and emerging hematopoietic progenitor cells to a mixture of FGF2, VEGF, IL6, SCF, TPO, IL3 under normoxia for about three days resulting in hematopoietic expansion to obtain a population of CD43$^+$ hematopoietic progenitors composed of CD43$^+$CD235a$^+$CD41a$^+$ erythromegakaryocytic progenitors and lin$^-$CD34$^+$CD43$^+$CD45$^{+/-}$ multipotent hematopoietic progenitors.

In some embodiments the mixture to be used in any of the preceding methods consists essentially of the mentioned components. In some embodiments the mixture to be used is xenogen-free.

In some embodiments the human pluripotente stem cells are provided on a substrate treated with Tenascin-C.

In a further aspect provided herein is a xenogen-free culture medium for differentiating human pluripotent stem cells, comprising IF9S medium supplemented with: about 50 to about 250 ng/ml BMP4; about 10 to about 15 ng/ml Activin A; about 10 to about 50 ng/ml FGF2; and about 1 mM to about 2 mM LiCl.

In a related aspect provided herein is a xenogen-free culture medium for differentiating human pluripotent stem cells, comprising IF9S medium supplemented with: about 10 to about 50 ng/ml FGF2; and about 20 to about 50 ng/ml VEGF. In some embodiments, where the medium contains FGF2 and VEGF, the medium also includes a hematopoietic cytokine. In some embodiments, the hematopoietic cytokine comprises: about 50 to about 100 ng/ml SCF; about 50 to about 100 ng/ml TPO; about 50 to about 100 ng/ml IL-6; and about 5 to about 15 ng/ml IL-3. In some embodiments, any of the foregoing media consist essentially of the IF9S medium and the supplemented components. In some embodiments, any of the foregoing media are provided in a concentrated form.

In another aspect provided herein is a xenogen-free cell culture system for differentiating human pluripotent stem cells into mesoderm, endothelial, and hematopoietic progenitor cells, comprising: human pluripotent stem cells seeded as a single cell suspension on a substrate comprising a layer of Tenascin C at a concentration of at least about 0.25 µg/cm$^2$ to 1 µg/cm$^2$; and a xenogen-free culture medium comprising IF9S medium supplemented with: about 50 to about 250 ng/ml BMP4; about 10 to about 15 ng/ml Activin A; about 10 to about 50 ng/ml FGF2; and about 1 to about 2 mM LiCl. In some embodiments the xenogen-free culture medium to be used in the xenogen-free cell culture system further comprises hematopoietic cytokines. In some embodiments the hematopoietic cytokines in the xenogen free medium comprise about 50 to about 100 ng/ml SCF, about 50 to about 100 ng/ml TPO, about 50 to about 100 ng/ml IL-6, and about 5 to about 15 ng/ml IL-3. In some embodiments the layer of Tenascin C is at a concentration of about 0.5 µg/cm$^2$.

In another aspect provided herein is a method of differentiating pluripotent stem cells, comprising the steps of: (a) providing human pluripotent stem cells; (b) seeding the cells as a single cell suspension on a substrate treated with Tenascin C; and (c) culturing the seeded cells in IF9S medium supplemented with BMP4, Activin A, FGF2, and LiCl under hypoxic conditions for a period of about two days to obtain about 30% $^{EMH}$lin$^-$KDR$^+$APLNR$^+$PDGFRalpha$^+$ primitive mesoderm cells with mesenchymoangioblast potential.

In some embodiments, the above method further comprises the step of culturing the cells at $^{EMH}$lin$^-$KDR$^+$ APLNR$^+$PDGFRalpha$^+$ primitive mesoderm stage in IF9S medium supplemented with FGF2 and VEGF under hypoxic conditions for about 1-2 days to obtain $^{EMH}$lin$^-$KDR$^+$ APLNR$^+$PDGFRalpha$^+$ primitive mesoderm with hemangioblast (HB-CFC) potential and $^{EMH}$linKDR$^{hi}$APLNR$^+$ PDGFRalpha$^{lo/-}$ hematovascular mesodermal precursors with a potential to form hematoendothelial clusters when cultured on OP9 cells.

In a further aspect provided herein are purified populations of cells generated by any of the foregoing methods for differentiating human pluripotent stem cells, wherein the cells have not been exposed to non-human constituents.

In a related aspect provided herein is a purified population of cells created by the methods described herein, wherein the cells are greater than about 35% $^{EMH}$lin$^-$KDR$^+$APLNR$^+$ PDGFRalpha$^+$ primitive mesoderm cells with a potential to form mesenchymoangioblast colonies.

In another aspect provided herein is a purified population of cells, wherein the cells are greater than about 35% of $^{EMH}$lin$^-$KDR$^+$APLNR$^+$PDGFRalpha$^+$ primitive mesoderm with hemangioblast (HB-CFC) potential and 30% $^{EMH}$lin$^-$KDR$^{hi}$APLNR$^+$PDGFRalpha$^{lo/-}$ hematovascular mesodermal cells with a potential to form hematoendothelial clusters when cultured on OP9 cells.

In a further aspect provided herein is a purified population of cells, wherein the population includes greater than about 40% of CD144$^+$ cells comprising CD144$^+$CD73$^-$CD235a/ 43$^-$ hemogenic endothelial progenitors (HEPs), CD144$^+$ CD73$^-$CD235a/CD43$^+$CD41a$^-$ angiogenic hematopoietic progenitors, and CD144$^+$CD73$^+$CD235a/43$^-$ non-hemogenic endothelial progenitors (non-HEPs).

In another aspect provided herein is a population of cells, wherein the population includes greater than about 30% CD43$^+$ hematopoietic progenitor cells composed of CD43$^+$ CD235a+CD41a$^+$ erythromegakaryocytic progenitors and lin$^-$CD34$^+$CD43$^+$CD45$^{+/-}$ multipotent hematopoietic progenitors.

In a further aspect provided herein is a method of producing mesenchymoangioblasts, comprising the steps of: (a) providing human pluripotent stem cells; (b) seeding the cells on a substrate treated with an effective amount of collagen; and (c) exposing the stem cells to a mixture comprising FGF2, BMP4, Activin A, and LiCl under hypoxic conditions for a period of about two days to form a population of $^{EMH}$lin$^-$KDR$^+$APLNR$^+$PDGFRalpha$^+$ primitive mesoderm cells with mesenchymoangioblast potential. In some embodiments the collagen to be used comprises Collagen IV.

In yet another aspect provided herein is a cell culture medium for differentiating human pluripotent stem cells, comprising: 64 mg/L L-Ascorbic Acid 2-Phosphate Mg$^{2+}$ salt, 40 µl/L monothioglycerol, 8.4 µg/L additional sodium selenite, 10 mg/L polyvinyl alcohol, 1× GLUTAMAX, 1× non-essential amino acids, 0.1× chemically-defined lipid concentrate, 10.6 mg/L Holo-Transferrin, and 20 mg/L insulin.

In a further aspect described herein is a method for differentiating human pluripotent stem cells comprising: (a) providing human pluripotent stem cells; and (b) culturing the human pluripotent stem cells under hypoxic conditions in a cell culture medium comprising FGF2, BMP4, Activin A, and LiCl for a period of about two days to form a cell population of $^{EMH}$lin$-$KDR+APLNR+PDGFRalpha+ primitive mesoderm cells with mesenchymoangioblast potential.

In some embodiments the human pluripotent stem cells are cultured on Tenascin C. In some embodiments the cell culture medium comprises an IF9S cell culture medium. In some embodiments the concentration, in the cell culture medium, of: BMP4 is about 50 ng/ml to about 250 mg/ml; Activin A is about 10 ng/ml to about 15 ng/ml; FGF2 is about 10 ng/ml to about 50 ng/ml; and LiCl is about 1 mM to about 2 mM.

In some embodiments the method further comprises (c) culturing, under hypoxic conditions, the cell population obtained in step (b) in a cell culture medium comprising FGF2 and VEGF for a period of about 1-2 days to obtain a cell population comprising $^{EMH}$lin$-$KDR+APLNR+PDG-FRalpha+ primitive mesoderm with hemangioblast (HB-CFC) potential and hematovascular mesoderm cells ($^{EMH}$lin$-$KDR$^{hi}$APLNR$^+$PDGFRalpha$^{lo/-}$) with a potential to form hematoendothelial clusters when cultured on OP9 cells. In some embodiments the concentration, in the cell culture medium, of FGF2 is about 10 ng/ml to about 50 ng/ml; and VEGF is about 20 ng/ml to about 50 ng/ml.

In some embodiments the method further comprises (d) culturing the hematovascular mesoderm cells of step (c), under hypoxic conditions, in a cell culture medium comprising FGF2, VEGF, IL6, SCF, TPO, and IL3 for about one day to obtain a cell population comprising CD144+CD73+ CD235a/CD43$-$ non-hemogenic endothelial progenitors (non-HEP), CD144+CD73$-$CD235a/CD43$-$ hemogenic endothelial progenitors (HEPs), CD144+CD73$-$CD235a/ CD43+41a$-$ angiogenic hematopoietic progenitors (AHP), and CD43+CD41a+ hematopoietic progenitor cells. In some embodiments the concentration, in the cell culture medium, of: FGF2 is about 10 ng/ml to about 50 ng/ml; VEGF is about 20 ng/ml to about 50 ng/ml; SCF is about 50 ng/ml to about 100 ng/ml; TPO is about 50 ng/ml to about 100 ng/ml; IL-6 is about 50 ng/ml to about 100 ng/ml, and IL-3 is about 5 ng/ml to about 15 ng/ml.

In some embodiments the method further comprises (e) culturing, under normoxia, the HEPs and hematopoietic progenitor cells in a culture medium comprising FGF2, VEGF, IL6, SCF, TPO, IL3 for about three days to obtain an expanded population of CD43+ hematopoietic progenitors comprising CD43$^+$CD235a$^+$CD41a$^+$ erythromegakaryocytic progenitors and lin$-$CD34$^+$CD43$^+$CD45$^{+/-}$ multipotent hematopoietic progenitors.

In some embodiments the method further comprises further coculturing the expanded population of CD34+CD43+ hematopoietic progenitors for a period of about three weeks on OP9 cells overexpressing DLL4 to obtain a cell population comprising CD4+CD8+ double positive T cells, wherein the human pluripotent stem cells of step (b) are cultured on a Tenascin C substrate.

In a related aspect provided herein is a method of differentiating human pluripotent stem cells, comprising at least one of: (i) culturing human pluripotent stem cells under hypoxic conditions in a cell culture medium comprising FGF2, BMP4, Activin A, and LiCl for a period of about two days to form a cell population of $^{EMH}$lin$^-$KDR$^+$APLNR$^+$ PDGFRalpha$^+$ primitive mesoderm cells with mesenchymoangioblast potential; (ii) culturing, under hypoxic conditions, $^{EMH}$lin$^-$KDR$^+$APLNR$^+$PDGFRalpha$^+$ primitive mesoderm cells with mesenchymoangioblast potential in a cell culture medium comprising FGF2 and VEGF for a period of about 1-2 days to obtain a cell population comprising $^{EMH}$lin$-$KDR+APLNR+PDGFRalpha+ primitive mesoderm with hemangioblast (HB-CFC) potential and hematovascular mesoderm cells ($^{EMH}$lin$^-$KDR$^{hi}$APLNR$^+$PDGFRalpha$^{lo/-}$) enriched in cells with a potential to form hematoendothelial clusters when cultured on OP9 cells; (iii) culturing hematovascular mesoderm cells ($^{EMH}$lin$^-$KDR$^{hi}$APLNR$^+$PDGFRalpha$^{lo/-}$) cells, under hypoxic conditions, in a cell culture medium comprising FGF2, VEGF, IL6, SCF, TPO, and IL3 for about one day to achieve formation of CD144+CD73+CD235a/CD43− non-hemogenic endothelial progenitors (non-HEP), CD144+CD73−CD235a/CD43− hemogenic endothelial progenitors (HEPs), CD144+CD73−CD235a/CD43+41a− angiogenic hematopoietic progenitors (AHP), and CD43+CD41a+ hematopoietic progenitor cells; (iv) culturing, under normoxia, hemogenic endothelial progenitors (HEPs) and CD43+CD41a+ hematopoietic progenitor cells in a culture medium comprising FGF2, VEGF, IL6, SCF, TPO, IL3 for about three days to obtain an expanded population of CD43+ hematopoietic progenitors comprising CD43+CD235a+CD41a+ erythromegakaryocytic progenitors and lin−CD34+CD43+CD45+/− multipotent hematopoietic progenitors; and (v) coculturing CD34+CD43+ hematopoietic progenitors for a period of about three weeks on OP9 cells overexpressing DLL4 to obtain a cell population comprising CD4+CD8+ T cells.

In another aspect provided herein is a cell culture medium suitable for hematoendothelial differentiation of human pluripotent stem cells, comprising a base medium, L-ascorbic acid 2-phosphate Mg2+ salt, monothioglycerol, additional sodium selenite, polyvinyl alcohol, Glutamax™, non-essential amino acids (NEAA), chemically defined lipid concentrate, Holo-Transferrin, and insulin.

In some embodiments the cell culture medium further comprises BMP4, Activin A, FGF2, and LiCl.

In other embodiments the culture medium further comprises FGF2 and VEGF.

In other embodiments the culture medium further comprises FGF2, VEGF, SCF, TPO, IL-6, and IL-3.

In some embodiments the cell culture medium comprises an IF9S medium. In some embodiments the IF9S cell culture medium has the IF9S cell culture medium formulation of Table 2.

In a related aspect provided herein is a 9S concentrated medium supplement, wherein dilution of the 9S concentrated medium supplement in an IMDM/F12 base medium yields an IF9S cell culture medium. In one embodiment is a kit comprising the 9S concentrated medium supplement, and one or more of BMP4, Activin A, FGF2, LiCl, SCF, TPO, IL-6, IL-3, and Tenascin C.

In a further aspect provided herein is a defined cell culture system for hematoendothelial differentiation of human pluripotent stem cells, comprising an IF9S cell culture medium and a Tenascin C substrate for adherent growth of human pluripotent stem cells or their differentiated progeny along the hematoendothelial lineage. In some embodiments the IF9S cell culture medium is maintained under hypoxic conditions. In some embodiments the defined cell culture system further comprises human pluripotent stem cells grown on the Tenascin C substrate.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A-4D Development of endothelial progenitors in cultures differentiated on CollV or TenC for 5 days in chemically defined conditions. (a) Flow cytometric analysis demonstrates major subsets of VE-cadherin+ (VEC; CD144+) progenitors generated after 5 days of hESC culture in chemically defined conditions on CollV and TenC. (b) Percentages of VEC+ (CD144+) cells and subsets generated in CollV and TenC cultures. Error bars are mean+SE from 3 experiments (*p<0.01). (c) CFC potential of isolated VEC+ (CD144+) subset in serum-free clonogenic medium with FGF2 and hematopoietic cytokines. (d) Endothelial and hematopoietic potential of day 5 VEC+ (CD144+) subsets. Progenitor subsets sorted and cultured in either endothelial conditions with subsequent tube formation assay, or on OP9 with immunofluorescent and flow cytometry results after 7 days. Scale bars, 100 μm.

DETAILED DESCRIPTION

Figure 1:
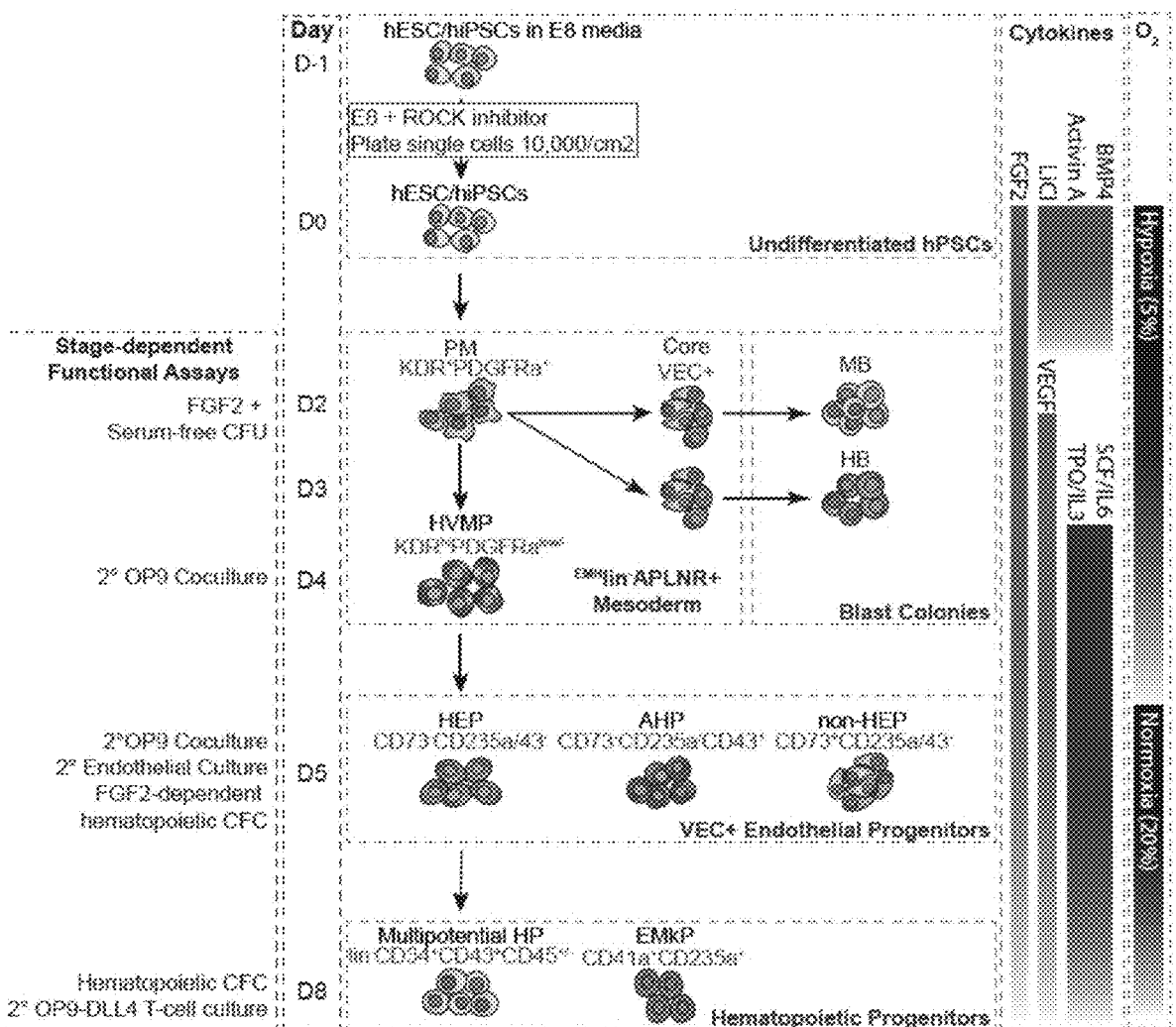
FIG. 1 Schematic diagram of hematopoietic differentiation. The diagram shows hematopoietic development pathways, specific markers and functional assays used to identify each stage of development, and conditions used for hPSC differentiation in chemically defined medium. Main cell subsets observed in prior differentiation studies using coculture with OP9 feeders and current chemically defined cultures are shown.

Human pluripotent stem cell (hPSC) technologies provide the opportunity to study human development in vitro and develop patient-specific blood cells without relying on HLA-matched donors. Previously, an efficient protocol for the differentiation of hematopoietic stem/progenitor cells using a coculture method on the mouse stromal cell line, OP9, was developed (Vodyanik, et al., 2005; Vodyanik, et al., 2006). This system reproduces primitive and definitive waves of hematopoiesis and can be used to obtain lin⁻ CD34⁺CD38⁻CD45RA⁻CD90⁺CD117⁺CD43⁺CD45⁻ᐟ⁺ multipotent definitive hematopoietic progenitors with HSC phenotype and lymphoid cells, including T and B cells (Carpenter, et al., 2011; Kutlesa, et al., 2009; Schmitt and Zuniga-Pflucker, 2002; Vodyanik, et al., 2005).

Human pluripotent stem cell coculture with OP9 cells induces mesendodermal and hemogenic endothelial differentiation. Upon plating hPSCs onto OP9 cells, the hPSCs begin to express the mesodermal marker apelin receptor (APLNR), VEGFR2 (KDR), and PDGFRalpha and acquire mesenchymoangioblast (MB) and hemangioblast (HB) potential (days 2-3 of differentiation). With advanced maturation, KDR⁺APLNR⁺ mesodermal cells upregulate KDR expression and downregulate PDGFRα, which is enriched in cells with the potential to form hematoendothelial clusters when cultured on OP9 cells.

At day 2-3.5 of differentiation, KDR⁺APLNR⁺ cells lack the typical Endothelial (CD31, VE-cadherin (CD144)), endothelial/Mesenchymal (CD73, CD105) and Hematopoietic (CD43, CD45) markers, i.e. have an $^{EMH}$lin⁻ phenotype. $^{EMH}$lin⁻ cells lack endothelial (CD31 and CD144), mesenchymal/endothelial (CD73, CD105), and hematopoietic (CD43 and CD45) markers, whereas lin⁻ cells lack markers of differentiated hematopoietic cells including CD2, CD3, CD4, CD8, CD11b, CD11c, CD14, CD15, CD16, CD19, and CD20. By day 4, VE-Cadherin⁺ (CD144) cells emerged. The emerging VE-cadherin⁺ cells represent a heterogeneous population, which includes CD144⁺CD235a/43⁻CD73⁺ non-hemogenic endothelial progenitors (non-HEPs), CD144⁺CD73⁻CD235a/43⁻ hemogenic endothelial progenitors (HEPs) and CD144⁺73⁻ CD43⁺CD235a⁺CD41a⁻, angiogenic hematopoietic progenitors. HEPs have the potential to give rise to multipotent lin⁻CD34⁺CD43⁺CD45⁺ᐟ⁻ hematopoietic progenitors.

Unfortunately, the OP9 system relies on mouse feeder cells and serum, which limit its utility for studying hPSC response to specific growth factors and manufacturing clinical grade therapeutic blood cells. In addition, the OP9 coculture system is very sensitive to variations in serum quality, stromal cell maintenance, and size of PSC colonies used for differentiation.

Although other investigators have developed feeder-free differentiation protocols, these protocols rely on forming embryoid bodies (EBs) for hematopoietic differentiation. EB methods often rely on serum and also have significant drawbacks, such as asynchronous differentiation and high variability. Recently several protocols have been developed to induce hematopoiesis in serum-free conditions (Salvagiotto, et al., 2011; Wang, et al., 2012); however, they still require xenogenic components, serum albumin, and/or proprietary supplements. It also remains unclear whether these protocols reproduce the distinct waves of hematopoiesis as seen on OP9.

In addition, most protocols differentiate hPSCs grown on MEFs or Matrigel®. Since a new, completely chemically-defined xenogen-free medium and matrix for hPSC-derivation and maintenance has been described (Chen, et al., 2011), there is a need to develop a similar chemically-defined xenogen-free directed differentiation protocol for deriving hematopoietic progenitors from hPSCs.

Unless defined otherwise in this specification, technical and scientific terms used herein have the same meaning as commonly understood by one of ordinary skill in the art to which this invention belongs and by reference to published texts.

It is to be noted that the term "a" or "an," refers to one or more, for example, "a molecule," is understood to represent one or more molecules. As such, the terms "a" (or "an"), "one or more," and "at least one" are used interchangeably herein. The term "about" as used herein contemplates a range of values for a given number of +/−10% the magnitude of that number. For example, "about 3 grams" indicates a value of 2.7 to 3.3 grams, and the like.

As referred to herein, the terms "defined conditions" or "defined medium" mean the identity and quantity of each ingredient is known. The term "ingredient," as used herein, refers to a component the molecular identity and quantity of which is known.

Disclosed herein are efficient and reproducible methods and supporting compositions that recapitulate, in a completely defined, xenogen-free system, the hematopoietic development observed in the OP9 co-culture system through early mesoderm, hematovascular mesoderm precursor, and hemogenic endothelial stages.

Table 1 provides a list of cell types, associated cell marker phenotypes, and corresponding abbreviations used herein.

human induced pluripotent stem cells (hiPSCs)) and (b) culturing the human pluripotent stem cells under hypoxic conditions in a cell culture medium comprising FGF2, BMP4, Activin A, and LiCl for a period of about two days to form a cell population of $^{EMH}$lin⁻KDR⁺APLNR⁺PDG-FRalpha⁺ primitive mesoderm cells with mesenchymoangioblast potential. Preferably, the human pluripotent stem cells are cultured without formation of embryoid bodies.

In some embodiments, the human pluripotent stem cells are plated at an initial density of about 5000 cells/cm² to about 15,000 cells/cm², e.g., 6000 cells/cm², 7000 cells/cm², 8000 cells/cm², 9000 cells/cm², or another plating density from about 5000 cells/cm² to about 15,000 cells/cm², In some embodiments, the differentiation method further includes the step of (c) culturing, under hypoxic conditions, the cell population obtained in step (b) in a cell culture medium comprising FGF2 and VEGF for a period of about 1-2 days to obtain a cell population comprising $^{EMH}$lin⁻

TABLE 1

Phenotypic features and definition of subsets with angiogenic and hematopoietic potential from hPSCs presented in the current application

| Abbreviation | Phenotype | Designation/Definition |
|---|---|---|
| PM A⁺P⁺ | $^{EHM}$lin⁻APLNR⁺PDGFRalpha GFR | Primitive posterior mesoderm (PM) enriched in cells expressing typical primitive streak and lateral plate/extraembryonic mesoderm genes. These cells have potential to form mesenchymoangioblast (MB) and hemangioblast (HB) colonies in serum-free medium in response to FGF2. |
| HVMP | $^{EHM}$lin⁻ APLNR⁺KDR$^{bright}$PDGFRalpha$^{low/-}$ | Hematovascular mesodermal precursor lacking the expression of primitive streak genes and highly enriched in bipotential hematoendothelial cluster forming cells. |
| HEP | CD144⁺CD235a/CD43⁻CD73⁻ | Hemogenic endothelial progenitors that have primary endothelial characteristics, lacking hematopoietic CFC potential and surface markers, but are capable of generating blood and endothelial cells upon coculture with stromal cells. |
| Non-HEP | CD144⁺CD235a/CD43⁻CD73⁺ | Non-hemogenic endothelial progenitors that have all functional and molecular features of endothelial cells and form endothelial colonies on OP9. |
| AHP | CD144⁺CD235a/CD43⁺CD73⁻ CD41a⁻ | Angiogenic blood progenitors that possess primary hematopoietic characteristics and FGF2 and hematopoietic cytokine-dependent colony-forming potential but are capable of generating endothelial cells. |
| | CD43⁺CD235a⁺CD41a⁺ | Hematopoietic progenitors enriched in erythromegakaryocytic progenitors. |
| | lin−CD34+CD43+CD45+/− | Multipotential hematopoietic progenitors with myelolymphoid potential |

Methods for Hematoendothelial Differentiation of Human Pluripotent Stem Cells (hPSCs)

Disclosed herein are methods for the differentiation of human pluripotent stem cells (either human embryonic or human induced pluripotent stem cells) under defined conditions, and, preferably, in the absence of embryoid body formation. At least one desired outcome of this differentiation is the provision of endothelial and hematopoietic cell populations that may be a source for functional studies of these lineages as well as a source for clinical therapies.

In some embodiments the differentiation method provided herein includes the steps of (a) providing human pluripotent stem cells (e.g., human embryonic stem cells (hESCs) or KDR⁺APLNR⁺PDGFRalpha⁺ primitive mesoderm with hemangioblast (HB-CFC) potential and hematovascular mesoderm cells ($^{EMH}$lin-KDR$^{hi}$APLNR⁺PDGFRalpha$^{lo/-}$) enriched in cells with a potential to form hematoendothelial clusters when cultured on OP9 cells. In further embodiments, the differentiation method further includes the step of (d) culturing the hematovascular mesoderm cells of step (c), under hypoxic conditions, in a cell culture medium comprising FGF2, VEGF, IL6, SCF, TPO, and IL3 for about one day to achieve formation of CD144⁺CD73⁺CD235a/CD43⁻ non-hemogenic endothelial progenitors (non-HEP), CD144⁺CD73⁻CD235a/CD43⁻ hemogenic endothelial progenitors (HEPs), CD144⁺CD73⁻CD235a/CD43⁺41a⁻ angiogenic hematopoietic progenitors (AHP), and CD43$^+$CD41a$^+$ hematopoietic progenitor cells.

In some embodiments, the differentiation method further includes the step of (e) culturing, under normoxia, the HEPs and hematopoietic progenitor cells in a culture medium comprising FGF2, VEGF, IL6, SCF, TPO, IL3 for about three days to obtain an expanded population of CD43$^+$ hematopoietic progenitors comprising CD43$^+$CD235a+ CD41a$^+$ erythromegakaryocytic progenitors and lin$^-$CD34$^+$ CD43$^+$CD45$^{+/-}$ multipotent hematopoietic progenitors.

In some embodiments a differentiation method disclosed herein includes the step of at least one of: (i) culturing human pluripotent stem cells, without embryoid body formation, under hypoxic conditions in a cell culture medium comprising FGF2, BMP4, Activin A, and LiCl for a period of about two days to form a cell population of $^{EMH}$lin$^-$KDR$^+$ APLNR$^+$PDGFRalpha$^+$ primitive mesoderm cells with mesenchymoangioblast potential; (ii) culturing, under hypoxic conditions, $^{EMH}$lin$^-$KDR$^+$APLNR$^+$PDGFRalpha$^+$ primitive mesoderm cells with mesenchymoangioblast potential in a cell culture medium comprising FGF2 and VEGF for a period of about 1-2 days to obtain a cell population comprising $^{EMH}$lin$^-$KDR$^+$APLNR$^+$PDGFRalpha$^+$ primitive mesoderm with hemangioblast (HB-CFC) potential and hematovascular mesoderm cells (EMH$^{lin-}$KDR$^{hi}$APLNR$^+$ PDGFRalpha$^{lo/-}$) enriched in cells with a potential to form hematoendothelial clusters when cultured on OP9 cells; (iii) culturing hematovascular mesoderm cells ($^{EMH}$lin$-$KDR$^{hi}$APLNR$^+$PDGFRalpha$^{lo/-}$) cells, under hypoxic conditions, in a cell culture medium comprising FGF2, VEGF, IL6, SCF, TPO, and IL3 for about one day to achieve formation of CD144$^+$CD73$^+$CD235a/CD43$^-$ non-hemogenic endothelial progenitors (non-HEP), CD144$^+$CD73$^-$ CD235a/CD43$^-$ hemogenic endothelial progenitors (HEPs), CD144$^+$CD73$^-$CD235a/CD43$^+$41a$^-$ angiogenic hematopoietic progenitors (AHP), and CD43$^+$CD41a$^+$ hematopoietic progenitor cells; and (iv) culturing, under normoxia, hemogenic endothelial progenitors (HEPs) and CD43$^+$CD41a$^+$ hematopoietic progenitor cells in a culture medium comprising FGF2, VEGF, IL6, SCF, TPO, IL3 for about three days to obtain an expanded population of CD43$^+$ hematopoietic progenitors comprising CD43$^+$CD235a+CD41a$^+$ erythromegakaryocytic progenitors and lin$^-$CD34$^+$CD43$^+$ CD45$^{+/-}$ multipotent hematopoietic progenitors.

In some embodiments, hypoxic conditions hypoxic conditions refer to a level of environmental oxygen (e.g., a cell culture incubator gas mixture) of about 3% 02 to about 10% 02. In some embodiments, hypoxic conditions is about 5% 02. In embodiments where a cell culture medium is allowed to equilibrate under hypoxic conditions, the cell culture medium becomes a hypoxic cell culture medium due to the lower level of dissolved oxygen compared to a cell culture medium equilibrated under normoxic conditions (e.g., a gas mixture containing about 20% oxygen).

In some embodiments, the culture medium to be used in any of the above-described differentiation methods comprises an IF9S medium, as described herein. In one embodiment, the IF9S medium to be used is the IF9S medium having the formulation set forth in Table 2.

In some embodiments, any of the above-referenced cells (e.g., human pluripotent stem cells) are cultured on Tenascin C. In some embodiments, any of the referenced cells are seeded on a substrate treated with an amount of Tenascin-C sufficient to adhere 10,000 cells/cm$^2$ to the substrate. In some embodiments, the Tenascin-C to be used is human Tenascin C. In some embodiments, the substrated is treated with Tenascin C at a concentration of at least about 0.25

µg/cm$^2$ to 1 µg/cm$^2$, e.g., 0.4 µg/cm$^2$, 0.5 µg/cm$^2$, 0.7 µg/cm$^2$, 0.8 µg/cm$^2$, or another concentration from at least about 0.25 µg/cm$^2$ to 1 µg/cm$^2$.

In some embodiments, in the cell culture medium to be used in the above-described differentiation methods, the concentration of: BMP4 is about 50 ng/ml to about 250 mg/ml; Activin A is about 10 ng/ml to about 15 ng/ml; FGF2 is about 10 ng/ml to about 50 ng/ml; LiCl is about 1 mM to about 2 mM; VEGF is about 20 ng/ml to about 50 ng/ml; SCF is about 50 ng/ml to about 100 ng/ml; TPO is about 50 ng/ml to about 100 ng/ml; IL-6 is about 50 ng/ml to about 100 ng/ml, and IL-3 is about 5 ng/ml to about 15 ng/ml.

In some embodiments, any of the above-referenced cells are cultured in a xeno-free cell culture medium. Of central importance for clinical therapies is the absence of xenogenic materials in the derived cell populations, i.e., no non-human cells, cell fragments, sera, proteins, and the like. Preferably, the present invention arrives at xenogen-free differentiated cells by use of Tenascin C or Collagen IV as a platform, which essentially replaces contact with OP9 cells used in earlier differentiation systems. In addition, the media disclosed herein are chemically-defined and, in some embodiments, are made xeno-free, and incorporate human proteins, which can be produced using recombinant technology or derived from placenta or other human tissues in lieu of animal-derived proteins. In some embodiments, all proteins added to the medium are recombinant proteins.

While differentiation processes include ordered, sequential events, the timing of the events may be varied by at least 20%. For example, while a particular step may be disclosed in one embodiment as lasting one day, the event may last for more or less than one day. For example, "one day" may include a period of about 18 to about 30 hours. Periods of time indicated that are multiple day periods may be multiples of "one day," such as, for example, two days may span a period of about 36 to about 60 hours, and the like. In another embodiment, time variation may be lessened, for example, where day 2 is 48+/−3 hours from d0; day 4 is 96+/−3 hours from d0, and day 5 is 120 hours+/−3 hours from d0.

Examples of potential committed and/or differentiated lineages obtainable by the present invention include KDR$^+$ APLNR$^+$PDGFRalpha$^+$ primitive mesoderm cells with HB and MB CFC potential, $^{EMH}$lin$^-$KDR$^{hi}$APLNR$^+$PDGFRalpha$^{lo/-}$ hematovascular mesoderm cells with potential to form hematoendothelial clusters when cultured on OP9 cells, VE-Cadherin$^+$ (CD144$^+$) subset cells, such as HEPs (CD144$^+$CD73$^-$CD235a/43$^-$, non-HEPS (CD144$^+$CD73$^+$ CD235a/43$^-$, and AHPs (CD144$^+$CD73$^-$CD235a/43$^+$41a$^-$), CD43$^+$ hematopoietic progenitor cells such as CD43$^+$ CD235a$^+$41a$^+$ erythromegakaryocytic hematopoietic progenitors, and lin$^-$CD34$^+$CD43$^+$CD45$^{+/-}$ multipotent hematopoietic progenitors. The term lineage$^-$ ("lin$^-$), as used herein, refers to a hematopoietic precursor or progenitor cell that has not have committed to any of its derivative blood cell lineages as of yet, since it retains the capability to differentiate into any of them. This characteristic is monitored by looking for the absence of cell surface markers indicative of differentiation into any of the derivative lineages. A further significant advantage of the present disclosure is the ability to use clonal cell populations due to the Tenascin C platform, which removes reliance on undefined stochastic events common to cell clumps, such as embryoid bodies, to generate differentiated populations. Moreover, the clonal cell populations exhibit greater uniformity during the differentiation process, which provides a higher yield of synchronized cells than previously seen in feeder cell systems. Therefore, the present disclosure also describes a more efficient, better scalable differentiation system than previously available.

Compositions

Defined Cell Culture Media and Concentrated Media Supplements

Some embodiments herein disclose a differentiation medium comprising a base medium, L-ascorbic acid 2-phosphate $Mg^{2+}$ salt, monothioglycerol, sodium selenite (in addition to any present in the base medium), polyvinyl alcohol, Glutamax™, non-essential amino acids (NEAA), chemically defined lipid concentrate, Holo-Transferrin, and insulin. Suitable base media for the differentiation media described herein include, but are not limited to, Iscoves Modified Dulbecco's Medium/F12 (IMDM/F12), TeSR1 base medium, which is mTeSR1™ base medium, (Stem Cell Technologies-see Ludwig and Thomson (2007), *Curr Protoc Stem Cell Biol.*, Chapter 1:Unit 1C.2 and U.S. Pat. No. 7,449,334) without FGF2 and TGF-beta; DF4S base medium, which is Essential 8™ medium (Life Technologies; also known as "E8" medium-see Chen and Thomson (2011), *Nat Methods*, 8(5):424-429 and U.S. Patent Application Publication No. 20120178166) without FGF2 and TGF-beta, I4S base medium, which is DF4S base with Iscove's modified Dulbecco's medium (IMDM) instead of DMEM/F12, and IF4S base is DF4S base with IMDM/F12 instead of DMEM/F12. Preferably, the base medium to be used is albumin-free. IMDM/F12 is a highly enriched synthetic medium suited for rapidly proliferating, high-density cell cultures with an added nutrient mixture.

In some embodiments, differentiation media used herein, referred to generically herein as "IF9S" media, comprises IMDM/F12, L-ascorbic acid 2-phosphate $Mg^{2+}$ salt, monothioglycerol, sodium selenite (in addition to any present in the base medium), polyvinyl alcohol, Glutamax™, non-essential amino acids (NEAA), chemically defined lipid concentrate (Life Technologies; Cat. No. 1905031), Holo-Transferrin, and insulin.

In one embodiment, an IF9S medium comprises IMDM/F12 (1×), L-ascorbic acid 2-phosphate $Mg^{2+}$ salt (64 mg/L), monothioglycerol (50 mg/L), sodium selenite (in addition to any present in the base medium; 8.4 ug/L), polyvinyl alcohol (10 mg/L), Glutamax™ (1×), NEAA (1×), chemically defined lipid concentrate (0.1×), Holo-Transferrin (10.6 mg/L), and insulin (20 mg/L).

As described herein, at various time points/stages of hematoendothelial differentiation of hPSCs, the complete differentiation medium to be used contains various combinations of cytokines, growth factors, and/or small molecules. Depending on the stage of hematoendothelial differentiation according to the methods described herein, a suitable complete differentiation medium will be supplemented with different combinations of cytokines with concentrations within the ranges described for the complete differentiation media described herein.

In some embodiments, complete differentiation medium comprises an IF9S medium, BMP4, Activin A, FGF2, and LiCl. In other embodiments complete differentiation medium comprises an IF9S medium, FGF2, and VEGF. In further embodiments, complete differentiation medium comprises an IF9S medium, FGF2, VEGF, SCF, TPO, IL-6, and IL-3. In some embodiments, the final complete medium concentration of: BMP4 is about 50 ng/ml to about 250 mg/ml; Activin A is about 10 ng/ml to about 15 ng/ml; FGF2 is about 10 ng/ml to about 50 ng/ml; LiCl is about 1 mM to about 2 mM; VEGF is about 20 ng/ml to about 50 ng/ml; SCF is about 50 ng/ml to about 100 ng/ml; TPO is about 50 ng/ml to about 100 ng/ml; IL-6 is about 50 ng/ml to about 100 ng/ml, and IL-3 is about 5 ng/ml to about 15 ng/ml. In some embodiments all of the proteins used in the complete differentiation medium are recombinant human proteins. In other embodiments, the complete differentiation medium comprises one or more non-human proteins (e.g., recombinant non-human proteins).

In some embodiments, a complete differentiation medium comprises an IF9S medium and one of the "cytokine" combinations listed in Table 3 at the indicated concentrations. In some embodiments, the IF9S medium formulation used in the just-mentioned complete differentiation media is the IF9S medium formulation set forth in Table 2.

While the presently disclosed media may include the specific morphogens, small molecules, and hematopoietic cytokines disclosed herein, it is contemplated that additional components with the same, equivalent, or similar properties may be used in addition to or in place of those disclosed, as are known in the art.

In some embodiments, media disclosed herein may include xenogenic (i.e., non-human, biologically derived) materials. For example, a xenogenic material may be a recombinant protein of xenogenic origin. Media disclosed herein may be also made in concentrated forms that are diluted prior to use, such as 2×, 10×, 100×, or 1000× concentrations.

Moreover, the replacement of certain xenogenic materials in the media of the present invention provided greater, unexpected benefits than just providing xenogen-free culture conditions. For example, it is believed that replacement of bovine serum albumin with polyvinyl alcohol led to a "thicker" medium that unexpectedly contributed to cell survival.

TABLE 2

| Description of an exemplary embodiment of an IF9S medium. | |
| --- | --- |
| IF9S Components | Concentration |
| IMDM/F12 | Base Component |
| L-ascorbic Acid 2-Phosphate $Mg^{2+}$ salt | 64 mg/L |
| monothioglycerol | 40 ul/L |
| additional sodium selenite | 8.4 ug/L |
| polyvinyl alcohol | 10 mg/L |
| GLUTAMAX | 1× |
| Non-essential amino acids | 1× |
| Chemically defined lipid concentrate | 0.1× |
| Holo-Transferrin | 10.6 mg/L |
| Insulin | 20 mg/L |

TABLE 3

| Day (hours ± range) (activity) | Cytokine | Concentration | Range | $O_2$ Level |
| --- | --- | --- | --- | --- |
| d0 (0 h) (change media) | BMP4 | 50 ng/ml | 50-250 ng/ml | Hypoxia (5% $O_2$, 5% $CO_2$) |
| | Activin A | 12.5 ng/ml | 10-15 ng/ml | |
| | FGF2 | 50 ng/ml | 10-50 ng/ml | |
| | LiCl | 2 mM | 1-2 mM | |

TABLE 3-continued

| Day (hours ± range) (activity) | Cytokine | Concentration | Range | O$_2$ Level |
|---|---|---|---|---|
| d2 (48 ± 3 h) | FGF2 | 50 ng/ml | 10-50 ng/ml | Hypoxia |
| (change media) | VEGF | 50 ng/ml | 20-50 ng/ml | |
| d4 (96 ± 3 h) | FGF2 | 50 ng/ml | 10-50 ng/ml | Hypoxia (d4) |
| (change media) | VEGF | 50 ng/ml | 20-50 ng/ml | |
| d5 (120 ± 3 h) | SCF | 50 ng/ml | 50-100 ng/ml | Normoxia (d5) |
| (move to normoxic | TPO | 50 ng/ml | 50-100 ng/ml | (20% O$_2$, 5% CO$_2$) |
| incubator) | IL-6 | 50 ng/ml | 50-100 ng/ml | |
| | IL-3 | 10 ng/ml | 5-15 ng/ml | |
| d6 (144 ± 3 h) | FGF2 | 50 ng/ml | 10-50 ng/ml | Normoxia |
| (add media) | VEGF | 50 ng/ml | 20-50 ng/ml | |
| | SCF | 50 ng/ml | 50-100 ng/ml | |
| | TPO | 50 ng/ml | 50-100 ng/ml | |
| | IL-6 | 50 ng/ml | 50-100 ng/ml | |
| | IL-3 | 10 ng/ml | 5-15 ng/ml | |

CytokineSupplement Combinations and Exemplary Concentrations at Different Days After Initiating Hematoendothelial Differentiation of hPSCs (in an IF9S medium).

Concentrated Medium Supplements

Also disclosed herein is a concentrated "9S" medium supplement, comprising L-ascorbic acid 2-phosphate Mg$^{2+}$ salt, monothioglycerol, additional sodium selenite, polyvinyl alcohol, Glutamax™ (or glutamine), non-essential amino acids (NEAA), chemically defined lipid concentrate, Holo-Transferrin, and insulin. In some embodiments, the concentrated 9S medium supplement comprises each component at a concentration 10× to 1000× of the final working concentration once diluted in a base medium. In some embodiments, the concentrations of all of the 9S components in the concentrated supplement is 10× to 1000× the concentrations listed in Table 3. In some embodiments, the supplement is to be diluted in IMDM/F12 medium to obtain IF9S medium as described herein.

Kits

Also contemplated herein are kits useful for hematoendothelial differentiation of hPSCs. In some embodiments, a kit comprises a 9S concentrated medium supplement, as described herein, one or more of BMP4, Activin A, FGF2, LiCl, SCF, TPO, IL-6, and IL-3, and instructions for generating an IF9S medium and a method for hematoendothelial differentiation of hPSCs as described herein. In some embodiments, a kit further includes IMDM/F12 medium. In some embodiments, the kit comprises a 9S concentrated medium supplement, Activin A, FGF2, LiCl, SCF, TPO, IL-6, IL-3, and instructions for generating an IF9S medium and a method for hematoendothelial differentiation of hPSCs as described herein. In further embodiments, any of the above-mentioned kits also include Tenascin C (e.g., human Tenascin C), which is used as a substrate for adhesive growth according the differentiation methods described herein.

Defined Cell Culture Systems for Hematoendothelial Differentiation of hPSCs

Also described herein is a defined cell culture system for hematoendothelial differentiation of hPSCs. Such cell culture systems include a defined differentiation culture medium as described herein, e.g., an IF9S medium, a Tenascin C protein substrate for adherent growth of hPSCs or their differentiated progeny along the hematoendothelial lineage. In some embodiments, Tenascin C is used at at least 0.25 μg/cm$^2$ to about 1 μg/cm$^2$ to generate a suitable adhesive substrate.

In some embodiments, the cell culture system includes an IF9S medium supplemented with BMP4, Activin A, FGF2, and LiCl. In some embodiments, the IF9S medium is supplemented with FGF2 and VEGF. In some embodiments, the IF9S medium utilized in the cell culture system is supplemented with FGF2, VEGF, SCF, TPO, IL6, and IL-3. In some embodiments, the IF9S medium used in the cell culture system is formulated according to the medium described in Table 2. In some embodiments, the defined cell culture system comprises a cell culture medium that is hypoxic, which is readily achieved by the use of a cell culture incubator permitting oxygen level regulation, and by equilibrating the cell culture medium in a cell culture incubator set to about 3% O$_2$ to about 10% O$_2$ (e.g., 5% O$_2$).

In further embodiments, the defined cell culture system further includes adherent human pluripotent stem cells cultured on the Tenascin C substrate in the IF9S medium according to the methods described herein.

Cells can be grown on, e.g., Tenascin C-coated cell culture dishes, multi-well cell culture plates, or microcarrier beads. Preferably, the Tenascin C protein is human Tenascin C (GenBank Accession No. CAA55309.1; available commercially, e.g., Millipore Cat. No. CC065)

Figure 10:
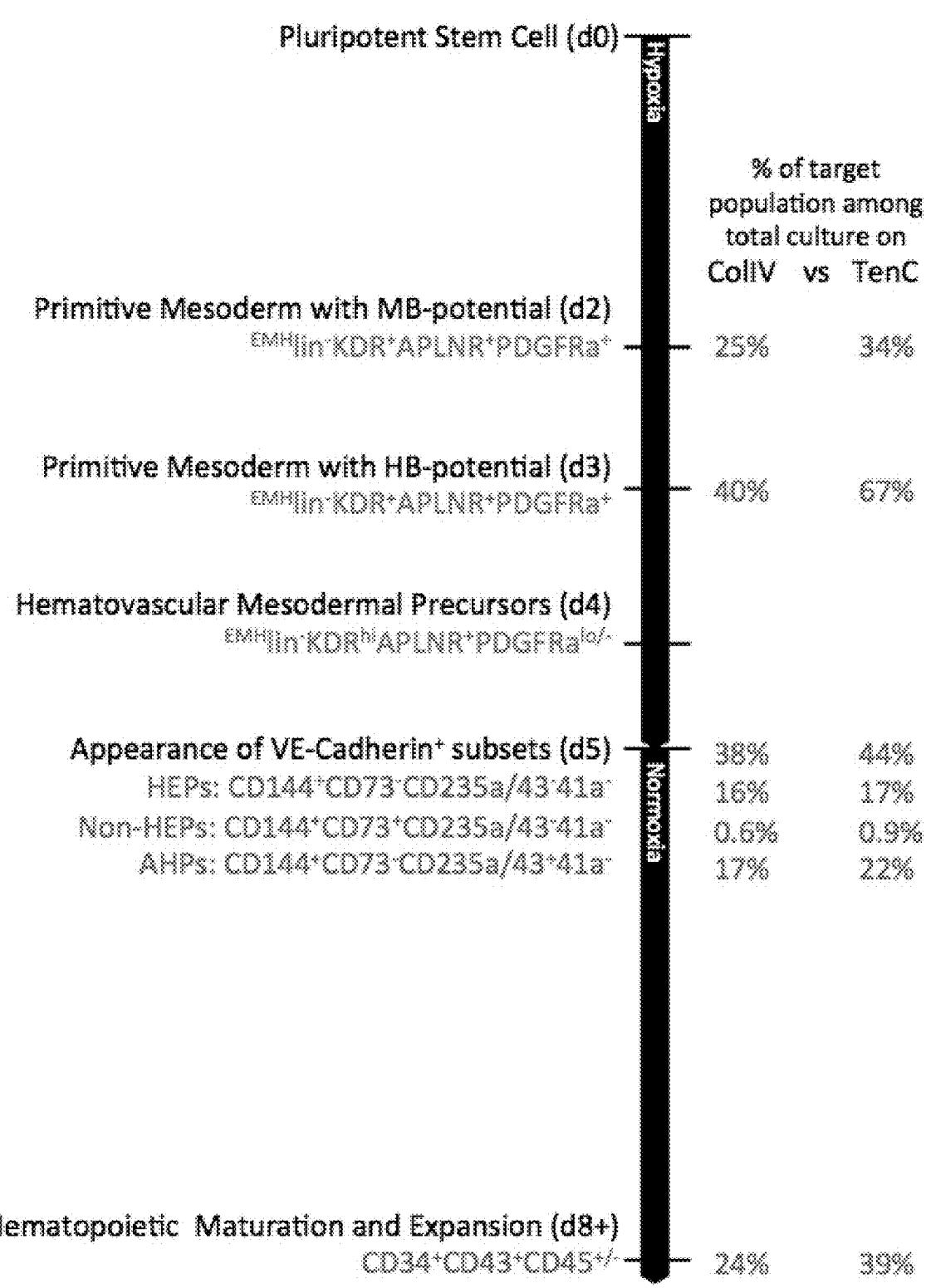
FIG. 10 is a diagram of a hematopoietic differentiation timeline comparing the efficiency of differentiation on Collagen IV vs. Tenascin C.

The use of Tenascin C and hypoxic conditions enables the generation of enriched populations of endothelial and hematopoietic cells at higher percentages than compared to cells seeded on Collagen IV or OP9 cells, such as greater than 10%, or greater than about 20%, greater than about 50%, or greater than about 60% when compared per stage per platform (see FIG. 10 and the Examples). In one embodiment, the percentages of target populations obtainable by the present invention may be greater than about 35% for KDR$^+$ APLNR$^+$PDGFRalpha$^+$ mesoderm cells or greater than about 20% of VE-Cadherin$^+$CD43$^-$ endothelial cells and greater than about 40% of CD34$^+$CD43$^+$ hematopoietic progenitor cells. Further, with respect to FIG. 10, the percentages of cells obtained on the Tenascin C platform are the indicated percentage or greater. Further, FIG. 10 represents the percentage of the target population (e.g., mesoderm progenitor, endothelial progenitor, hematopoietic progenitors with the corresponding phenotypes as according to flow cytometry) of the total culture when differentiated on either Col IV or TenC.

The present methods and materials may be combined into cell culture systems to provide new differentiation platforms. In one embodiment, a basic cell culture system includes pluripotent stem cells seeded on Tenascin C. In another embodiment, a cell culture system includes stem cells seeded on Collagen IV, in a medium supplemented with Activin A. These systems have the capacity to produce cell populations enriched with hematopoietic progenitor cells.

The cell culture systems contemplated herein may be modular, in that they may incorporate additional components that alter the resulting cell populations derived from the system. For example, the cell culture system may incorporate media that are xenogen-free for certain desired outcomes. However, they may include xenogen-containing media if, for example, clinical therapies are not envisioned for the derived cell populations. Further, the cell culture systems may be based on various sized culture vessels, as are known in the art, to arrive at the desired cell population production scale.

In some cases, one can substitute some of the components of an IF9S medium. For example, ascorbic acid and mono-thioglycerol can be replaced with an optional supplement of a compound and/or a thiol-containing compound with anti-oxidant properties. GLUTAMAX™ can be replaced with an optional supplement of L-glutamine. "Non-essential amino acids (NEAA)," which is a general term for amino acids that the human body can produce from other amino acids can be replaced with an optional supplement of amino acids. "Chemically defined lipid concentrate," which is a solution specifically distributed by Life Technologies, can be replaced with an optional supplement of lipids. Additional selenite, insulin, and holo-transferrin can be replaced with any ITS supplement. ITS stands for "Insulin-Transferrin-Selenite." Some companies (e.g., Life Technologies), sells ITS solutions to be used as supplements in other basal media (DMEM, for example). However, the manufacturer does not provide concentrations for each component. Polyvinyl alcohol can be replaced with an optional supplement of a biologically inactive media thickening compound.

The following examples set forth preferred materials and methods for accomplishment of the invention. It is to be understood, however, that these examples are provided by way of illustration and nothing herein should be taken as a limitation upon the overall scope of the invention.

EXAMPLES

Example 1 IMDM/F12 Based Media Significantly Improves Differentiation Efficiency of hPSCs into Hematoendothelial Lineage Previously, our lab developed protocol for the efficient differentiation of hematopoietic hPSC differentiation using a coculture method on the mouse stromal cell line, OP9.[9,13] Although OP9 system supports efficient generation of HE and multilineage hematopoietic progenitors (FIG. 1), this system is very sensitive to variations in serum quality, stromal cell maintenance, and size of hPSC colonies and clumps used for differentiation.[13,14] Forming embryoid bodies (EBs) is another commonly used approach for inducing HE and blood formation from hPSCs.[7,15,16] However, EB methods often rely on serum or non-defined medium and also have significant drawbacks, such as asynchronous differentiation, high variability and dependence on initial clump size. Additionally, inconsistency in quality of hPSCs due to variations in albumin batches used for hPSC maintenance may introduce variations in efficiency of blood production.

To overcome these limitations we decided to identify chemically defined medium and matrix proteins capable to support hematoendothelial differentiation without serum from single cell suspension of H1 human embryonic stem cells (hESCs) expanded in E8 completely defined xenogene-free medium on vitronectin (VTN)[17].

Methods

Human Pluripotent Stem Cell Maintenance

Human pluripotent stem cells (H1 and H9 hESCs, fibroblast derived iPSC 19-9-7T, and BM119-9 iPSCs derived from bone marrow mononuclear cells) were maintained on vitronectin or matrigel in E8 media made in-house supplemented with FGF2 and TGFβ (Peprotech). Cells were passaged when they reached 80% confluency using 0.5 mM EDTA in PBS. The cells were maintained in normoxic conditions with 5% $CO_2$.

Human Pluripotent Stem Cell Differentiation

Human pluripotent stem cells were detached from vitronectin or matrigel when they reached 80% confluency using 1× TrypLE (Life Technologies) and plated at an optimized density ranging from 5000 cells/cm² to 15,000 cells/cm² depending on the cell line onto 6-well plates coated with 0.5 µg/cm² of CollV (Sigma-Aldrich) or 0.5 µg/cm² Tenascin-C (Millipore) in E8 media supplemented with 10 µM Rho Kinase inhibitor (Tocris Y-27632). After 24 hours (day 0), the media was changed to IF9S media supplemented with 50 ng/ml BMP4 (Peprotech), 15 ng/ml Activin A (Peprotech), 50 ng/ml FGF2 (Miltenyi Biotech), 2 mM LiCl (Sigma), and on occasion, 1 µM Rho Kinase inhibitor to increase cell viability. On day 2, the media was changed to IF9S media supplemented with 50 ng/ml FGF2 and 50 ng/ml VEGF, and 10 µM SB-431542 (Tocris) where mentioned. On day 4, the media was changed to IF9S media supplemented with 50 ng/ml FGF2, VEGF, TPO, SCF, IL-6, and 10 ng/ml IL-3. On day 6, additional IF9S media supplemented with the same 6 factors were added to the cultures without aspirating the old media (Table 3 Table 3). IF9S (IMDM/F12 with 9 supplements) was made in-house with the following: 50% IMDM 50% F12 (Life Technologies) supplemented with 64 mg/L L-ascorbic Acid 2-Phosphate Mg2+ salt (Sigma-Aldrich), 40 ul/L monothioglycerol (Sigma-Aldrich), 8.4 µg/L additional sodium selenite (Sigma-Aldrich), 10 mg/L polyvinyl alcohol (Sigma-Alderich), 1× glutamax (Life Technologies), 1× non-essential amino acids (Life Technologies), 0.1× chemically defined lipid concentrate (Life Technologies), 10.6 mg/L Holo-Transferrin (Sigma-Aldrich), and 20 mg/L Insulin (Sigma-Aldrich) (Table 2). Differentiation was conducted in hypoxic condition from day 0 to day 5, and transferred to normoxic condition from day 6 to day 9 (FIG. 1). The 1× TrypLE was used to dissociate and collect cells for analysis.

Mesenchymo- (MB) and Hemangioblast (HB) Assay

MB and HB were detected using serum-free CFC medium supplemented with FGF2 assay as previously described[11]. Day 2 or 3 cultures were dissociated and prepared in a single-cell suspension using 1× TrypLE (Life Technologies) and 5,000 cells of the total culture were plated into the CFC media. MB and HB colonies were scored 12 days after plating the single-cell suspension.

Hematopoietic CFC Assay.

Hematopoietic CFC were detected using serum-containing H4436 Methocult™ supplemented with human recombinant SCF, G-CSF, GM-CSF, IL-3, IL-6, and EPO (Stem Cell Technologies). Hematopoietic potential of AHPs was evaluated using serum-free SF H4236 methocult with added FGF2 (20 ng/ml), SCF (20 ng/mL), IL3 (10 ng/mL), IL6 (10 ng/mL), and EPO (2 U/mL) (Stem Cell Technologies) as previously described[6]. 1000-10000 differentiated cells were plated into the CFC medium and the colonies were scored after 14 days of culture.

Flow Cytometry and FACS

Flow Cytometry was conducted using the using a FACSCalibur flow cytometer and following antibodies: CD31-FITC (clone WM59), CD34-FITC (8G12), CD41a-

FITC/APC (clone HIPS), CD43-FITC/PE/APC (clone 1G10), CD45-APC (clone HI30), CD73-FITC/PE (clone AD2), CD144-FITC/PE/AlexaFluor647 (clone 55-7H1), CD235a-FITC/PE/APC (clone GA-R2), KDR-PE/AlexaFluor647 (clone 89106), PDGFRα-PE (clone aR1) (BD Biosciences), TRA-1-85-FITC/PE (clone TRA-1-85), and APLNR-APC (clone 72133) (R&D Systems). Sorting was conducted on a FACS Aria, as described previously 46. The purity of isolated populations was 92-95%.

Secondary Culture of Differentiated hPSCs onto OP9

OP9 cells were maintained in α-MEM (Gibco) supplemented with 20% FBS (Hyclone) as previously described.[10] Sorted day 4 or day 5 cultures were plated on a confluent layer of OP9 cells in α-MEM (Gibco) supplemented with 10% FBS (Hyclone) supplemented with 100 μM MTG, 50 μg/ml ascorbic acid, 50 ng/ml SCF, TPO, IL-6, and 10 ng/ml IL-3 at a density of 5,000 cells/well of a 6 well plate as previously described[6]. Cultures were prepared for flow cytometry 4 to 7 days later by collecting floating cells and dissociating the entire cultures using 1× TrypLE.

T-Cell Differentiation of Day 9 Cultures

An OP9 cell line (OP9-DLL4) constitutively expressing human delta-like ligand 4 (DLL4) was established by our lab using lentivirus and was maintained similarly to OP9. After human pluripotent stem cells were differentiated for 9 days, the floating cells were collected, strained through a 70 μm cell strainer (BD Biosciences) and washed. Then, they were resuspended in T-cell differentiation media consisting of α-MEM (Gibco) supplemented with 20% FBS (Hyclone) supplemented with IL7 (5 ng/ml), Flt3L (5 ng/ml) and SCF (long/ml). Then, they were plated on an OP9-DLL4 and cultured at 37° C. and 5% CO2. After 4 days, the cells were harvested using collagenase IV (Gibco) solution (1 mg/ml in DMEM/F12, Gibco) and 1× TrypLE (Invitrogen), and passaged onto a fresh layer of OP9-DLL4. After 3 days, the cells are passaged again. Subsequent passages are conducted every 7 days up to 4 weeks, after which the floating cells are collected for flow analysis and genomic DNA extraction for TCR rearrangement assay.

TCR Rearrangement Assay

Genomic DNA was isolated using quick-gDNA MiniPrep (Zymo Research). TCRβ and TCRγ clonality was detected using a PCR amplification kit (Invivoscribe) and AmpliTaq Gold® DNA polymerase (Applied Biosystems) as previously described[33]. The PCR products were analysed by heteroduplex analysis on a 6% polyacrylamide gel stained with ethidium bromide.

Microarray Analysis of Mouse Stromal Cell Lines

A mouse bone marrow stromal cell line, OP9, was obtained from Dr. Toni Nakano (Research Institute for Microbial Diseases, Osaka University, Japan), S17 was obtained from Dr. Kenneth Dorshkind (University of California, Los Angeles) and MS-5 was obtained from the German Tissue Culture Collection. Stromal cell lines were cultured as described[9]. DNA-free RNA was isolated using RiboPure™ RNA and DNAse using TURBO™ DNAfree reagents (Ambion). All samples were processed at the Gene Expression Center of the Biotechnology Center at the University of Wisconsin, Madison and analyzed using A4543-00-01 MM8 60mer expr Mus musculus 1-Plex Array standard arrays manufactured by NimbleGen Systems (Madison, WI). Gene expression raw data were extracted using NimbleScan software v2.1. Considering that the signal distribution of the RNA sample is distinct from that of the gDNA sample, the signal intensities from RNA channels in all eight arrays were normalized with a Robust Multiple-chip Analysis (RMA) algorithm[47]. Separately, the same normalization procedure was performed on those from the gDNA samples. For a given gene, the median-adjusted ratio between its normalized intensity from the RNA channel and that from the gDNA channel was then calculated as follows: Ratio=intensity from RNA channel/(intensity from gDNA channel+median intensity of all genes from the gDNA channel). Genes with more than 3 fold differences in expression were considered differentially expressed. Only genes with expression level >1 were selected for analysis.

Results

Figure 8:
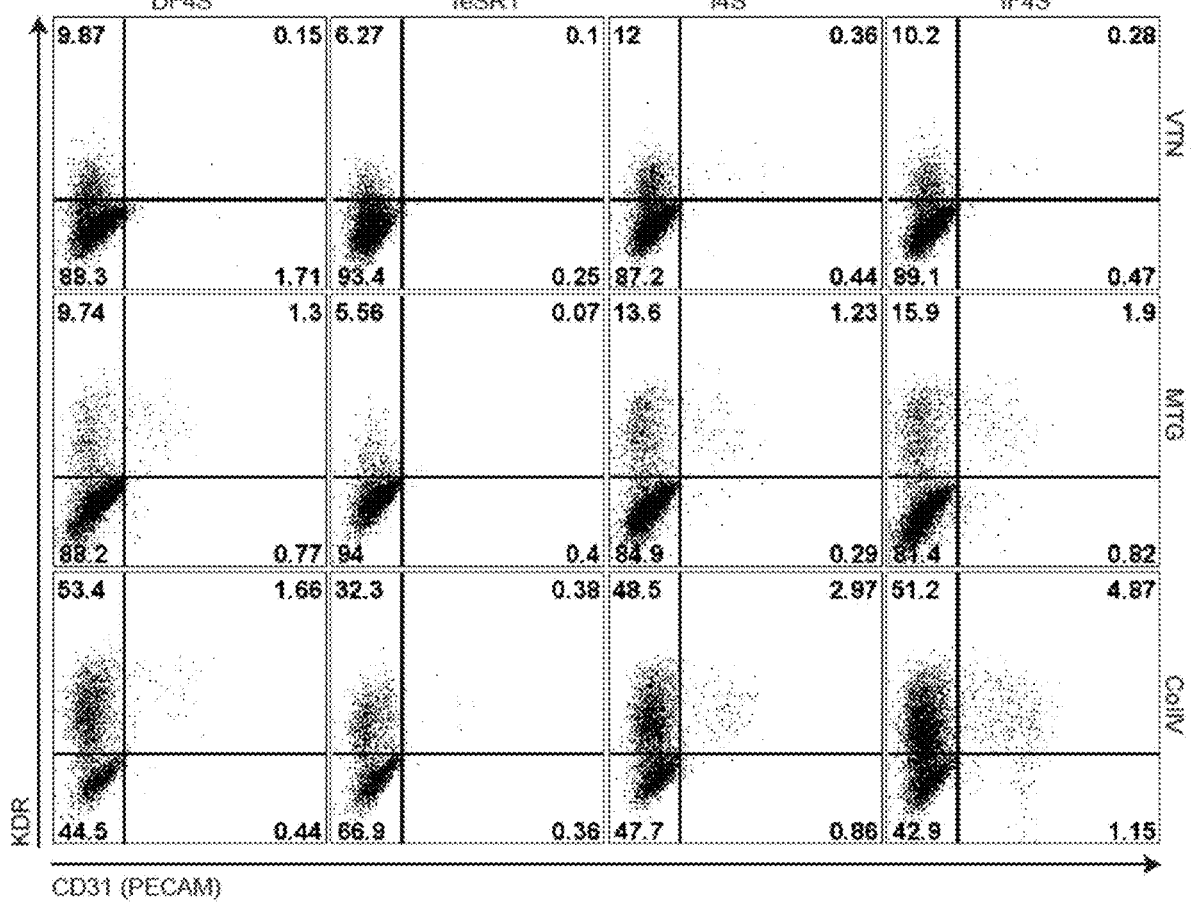
FIG. 8 Generation of $KDR^{hi}CD31^+$ hematoendothelial progenitors in cultures using different basal media and matrix protein. TeSR1 base medium is TeSR1 without cytokines. DF4S is DMEM/F12-based media supplemented with 4 supplements; 64 mg/L L-ascorbic Acid 2-Phosphate $Mg^{2+}$ salt, 8.4 μg/L sodium selenite, 10.6 mg/L Holo-Transferrin, and 20 mg/L Insulin. I4S is DF4S with IMDM-based media instead of DMEM/F12-based media, but with the four previously mentioned supplements. IF4S is DF4S with IMDM/F12-based media instead of DMEM/F12-based media, but with the 4 previously mentioned supplements. VTN is vitronectin matrix; MTG is Matrigel® substrate; ColIV is Collagen IV matrix. Flow cytometry plots show percent of $KDR^{hi}CD31^+$ endothelial precursors of day 4 cells differentiated in each media supplemented with 50 ng/ml FGF2, BMP4 and VEGF in hypoxic conditions.

IMDM/F12 Based Medium Significantly Improves Differentiation Efficiency of hPSCs into the Hematoendothelial Lineage We plated hESCs as single cells and allowed to attach over 24 hours in E8 media supplemented with 10 μM Rho kinase inhibitor on Matrigel (MTG), VTN, or Collagen IV (ColIV). Then, the media was changed to one of three basal media free of animal proteins, or growth factor-free TeSR1, supplemented with human recombinant BMP4, FGF2, and VEGF factors which commonly used to induce blood formation from hPSCs[18,19]. After 4 days of differentiation cell cultures evaluated for the presence of KDR[hi]CD31[+] cells which are highly enriched in hematoendothelial progenitors[6]. Flow cytometry analysis showed that cells differentiated on ColIV-coated plates in IMDM/F12 media supplemented with L-ascorbic Acid 2-Phosphate Mg$^{2+}$ salt, 8.4 μg/L additional sodium selenite, Holo-Transferrin, and insulin differentiated most efficiently into KDR[hi]CD31[+] hematoendothelial precursors (FIG. 8). Later, we found that the addition of polyvinylalcohol, NEAA, Glutamax, chemically defined lipid concentrate, and monothioglycerol increased cell viability and differentiation efficiency (data not shown). The subsequent basal media is referred to as IF9S (IMDM/F12 plus 9 supplements). These results demonstrated that the selected media and supplements made it possible to obtain hematoendothelial cells in a chemically defined, xenogenefree conditions on ColIV matrix from hPSCs maintained in E8 media.

Figures 2A, 2B:
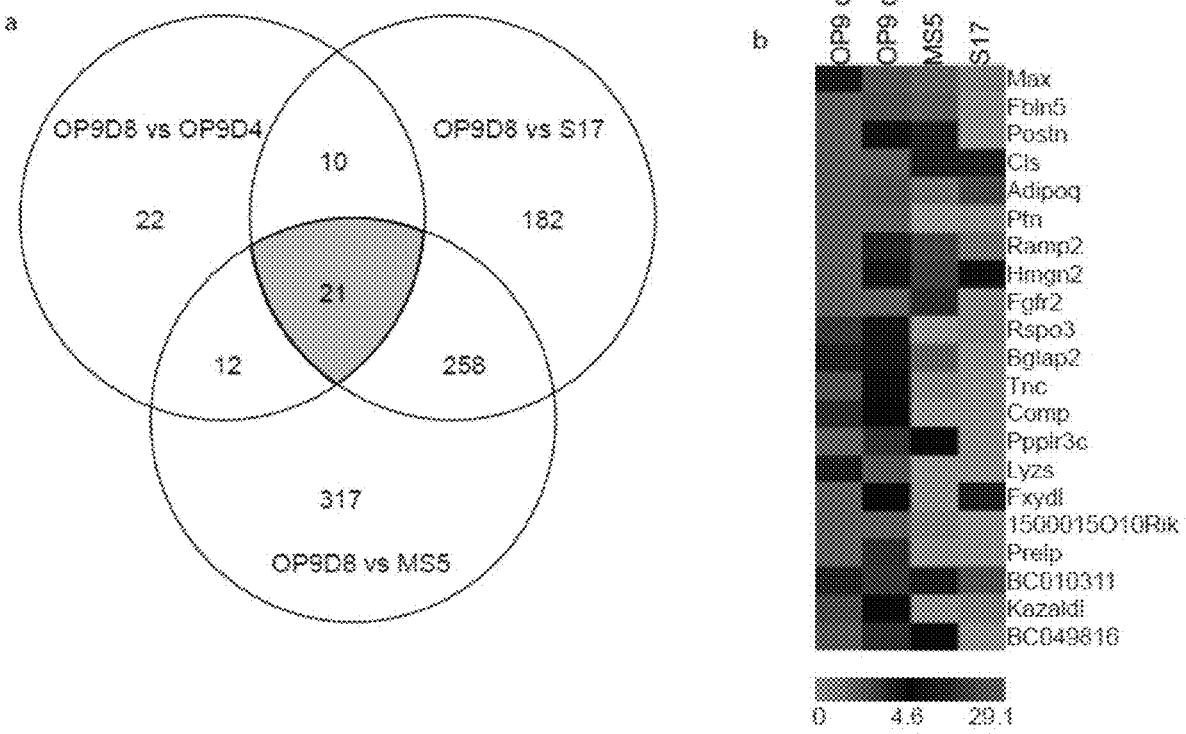
FIGS. 2A-2B Identification of a unique molecular signature of overgrown OP9 stromal cells. (a) Venn diagram showing the overlap between differentially expressed genes in overgrown OP9 day 8 versus freshly confluent OP9 day 4, and MS5 and S17. 21 genes marked with gray background are uniquely overexpressed in day 8 OP9 cells as compare to all other tested cell lines. (b) Heat map of differentially expressed overlapping genes as shown in (a). Tenascin-C (Tnc) is one of the top differentially overexpressed genes in over-confluent OP9 cells.

Example 2 Analysis of a Unique Molecular Signature of Hematopoiesis-Supportive Stromal Cells Identified Tenascin C as an Extracellular Matrix that Promotes the Development and Maintenance of Hematopoietic Precursors Previously, we showed that OP9 is superior to other stromal cell lines such as S17, and MS5 in induction of hematopoietic differentiation[9]. It was also found that day 8 overgrown OP9 cultures are superior to day 4 freshly confluent OP9 in induction of hematopoietic-CFCs, including multipotential GEMM-CFCs[9]. Since the confluency of the stromal cells affect differentiation efficiency, this led us to believe that there is an extracellular matrix influencing hematoendothelial differentiation. In order to find the matrix protein(s) critical for hematopoiesis-supportive activity of OP9 we performed molecular profiling of S17 and MS5 stromal cell lines with low hematopoiesis-inducing potential and OP9 cells. In addition, we compared overgrown OP9 (day 8) with freshly confluent OP9 (day 4) monolayers. Transcriptome analysis revealed 21 genes differentially expressed in day 8 overgrown OP9 cells as compared to all other stromal cells (FIG. 2a). These included genes encoding Ptn (pleiotrophin), a secreted regulator of HSC expansion and regeneration,[20] Rspo3 (R-spondin 3), an important regulator of Wnt signaling and angioblast development[21], and an extracellular matrix proteins Postn (periostin) required for B lymphopoiesis,[22]. Interestingly, one gene that showed the most significant expression change in overconfluent OP9 was Tnc (Tenascin C) (FIG. 2b). TenC is expressed in mesenchymal cells underlying hematopoietic clusters in the Aorta-Gonado-Mesonephros (AGM) region and is required for intraembryonic and postnatal hematopoiesis[23-25]. It is also expressed in the bone marrow stem cell niche[25]. Because of these unique properties, we tested whether TenC could support hematopoietic differentiation more effectively than ColIV.

Example 3 Time- and Dose-Dependent Treatment of FGF2, BMP4, Activin a, LiCl, and VEGF Induces Mesodermal, Endothelial, and Hematopoietic Stages of Development Our prior studies identified distinct stages of hematoendothelial development following hPSC differentiation in coculture with OP9 (FIG. 1)[6,9-11,26]. Plating hPSCs onto OP9 stromal cells induces formation of primitive streak and mesodermal cells which can be detected based on expression apelin receptor (APLNR) and KDR (VEGFR2)[11] and lack of expression Endothelial (CD31, CD144 (VE-cadherin)), endothelial/Mesenchymal (CD73, CD105) and Hematopoietic (CD43, CD45) markers, i.e. by $^{EMH}$lin– phenotype. The first KDR$^+$ mesodermal cells appearing in OP9 coculture on day 2 of differentiation express APLNR and PDGFRalpha ($^{EMH}$lin$^-$KDR$^+$APLNR$^+$PDGFRalpha$^+$ hereafter referred as A$^+$P$^{3+}$ cells). These cells display mesenchymoangioblast (MB) potential, i.e. capacity to form colonies with both mesenchymal stem cell (MSC) and vascular potential. On day 3 of differentiation A$^+$P$^{3+}$ cells acquire blast (BL)-CFC or hemangioblast (HB) potential[11]. Both MB and HB potentials can be detected using colony-forming assay in serum-free clonogenic medium supplemented with FGF2[11]. With advanced maturation, mesodermal cells loss BL-CFC activity and upregulate KDR expression and downregulate PDGFRalpha, i.e. acquire KDR$^{hi}$APLNR$^+$PDGFRalpha$^{lo/-}$ hematovascular progenitor (HVMP) phenotype which enriches in cells with the potential to form hematoendothelial clusters on OP9[6]. The endothelial stage of development is defined by expression of endothelial-specific marker VE-cadherin (CD144). The first VE-Cadherin$^+$ (CD144$^+$) cells emerge from KDR$^{hi}$APLNR$^+$PDGFRalpha$^{lo/-}$ mesodermal cells by day 4 of differentiation. The emerging VE-cadherin$^+$ (CD144+) cells represent a heterogeneous population which include CD43$^-$CD73$^+$ (CD144$^+$CD43$^-$CD73$^+$) non-hemogenic endothelial progenitors (non-HEPs) and CD43$^-$ CD73$^-$ (CD144$^+$CD43$^+$CD73$^-$) hemogenic endothelial progenitors (HEPs)[6]. HEPs lacking hematopoietic CFC potential, but acquire it after culture with stromal cells. The hematopoietic stage of development is defined by expression of hematopoietic-specific marker CD43[6,10]. The first CD43$^+$ cells emerge within VE-cadherin$^+$ (CD144+) cells on day 4-5 of differentiation. These cells express low level CD43 and coexpress CD235a, but lack CD41a expression, i.e. had CD144$^+$CD43/235a$^+$41a$^-$ phenotype. Because these cells have capacity to form hematopoietic colonies in presence of FGF2 and hematopoietic cytokines as well to grow endothelial cells on fibronectin, we designated them as angiogenic hematopoietic progenitors (AHPs). The first CD41a cell appears within CD235a positive cells. CD235a$^+$CD41a$^+$ cells are highly enriched and erytho-megakaryocytic progenitors and lacking endothelial potential. The progenitors with broad myelolymphoid potential and lin$^-$CD34$^+$CD43$^+$ CD45$^{+/-}$ phenotype can be detected in hPSC cultures shortly after emergence of CD235a$^+$CD41a$^+$ cells. Acquisition of CD45 expression by lin$^-$ cells is associated with progressive myeloid commitment.[10]

Figures 3A, 3B, 3C, 3D:
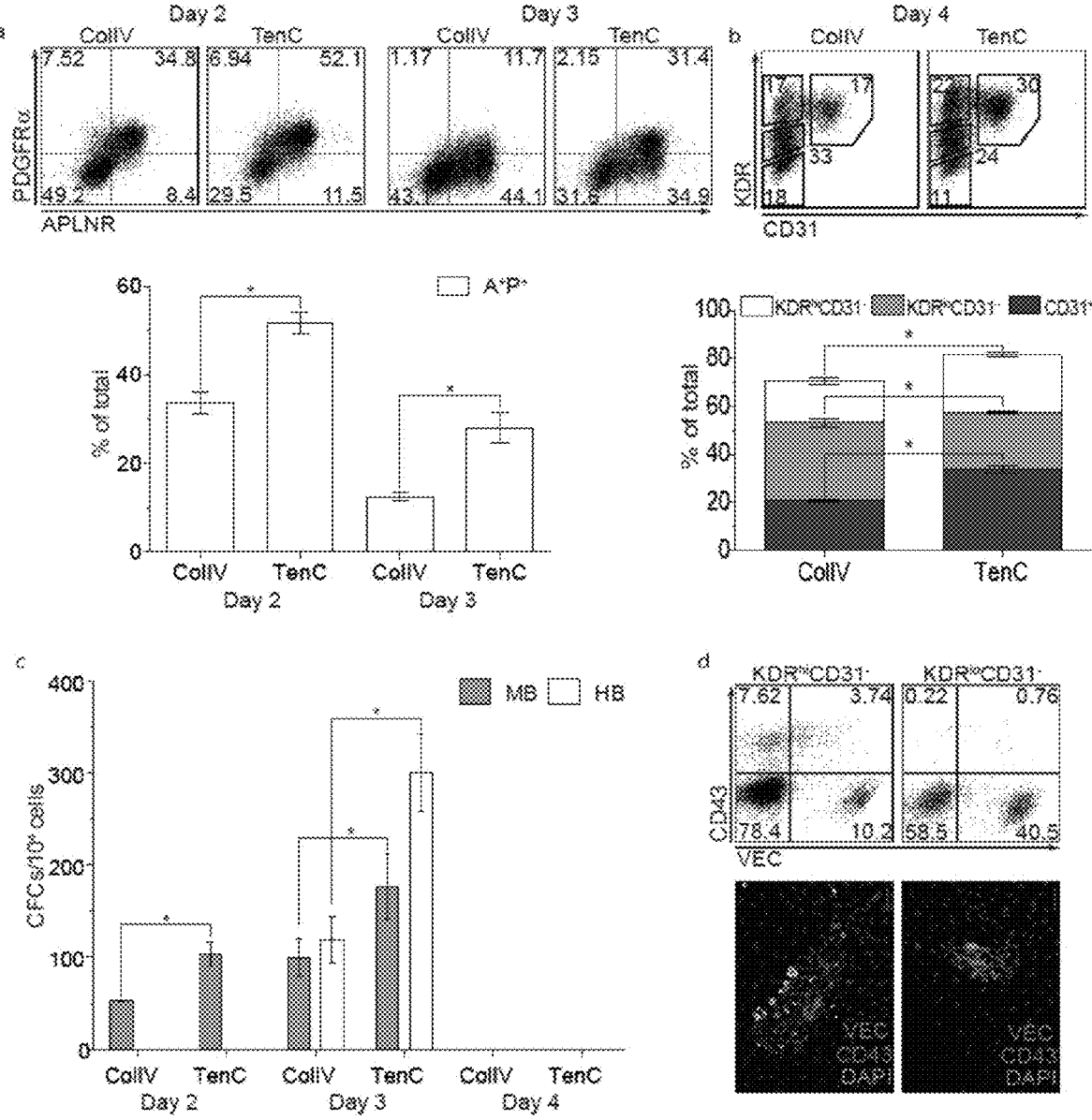
FIGS. 3A-3D Mesodermal development in hESC cultures differentiated on CollV vs TenC for 2, 3, and 4 days in chemically defined conditions. (a) Flow cytometry plots and graphs comparing percentage of $^{EMH}$lin$^-$KDR$^+$APLNR$^+$PDGFRalpha$^+$ (A+P+) primitive mesodermal population on days 2 and 3. (b) Flow cytometry plots and graphs comparing percentage of KDR$^{hi}$CD31$^-$ (HVMP), CD31$^+$, and KDR$^{lo}$CD31$^-$ populations on day 4. (c) Comparison of MB/HB-colony forming potential of day 2, day 3, and day 4 cultures. (d) Hematopoietic and endothelial potentials of KDR$^{hi}$CD31$^-$ and KDR$^{lo}$CD31$^-$ cells isolated from day 4 cells differentiated in chemically defined conditions after coculture with OP9 for 7 days. Upper panels show flow cytometry of TRA-1-85+ gated human cells and lower panels shows immunofluorescence staining of cells from OP9 cocultures with KDR$^{lo}$CD31$^-$ and KDR$^{lo}$CD31$^-$ cells. (a), (b), and (c) bars are mean+SE from 3 experiments (*p<0.01).

To reproduce the hematoendothelial program observed in OP9 coculture we decided to select the optimal combinations of morphogens for mesoderm induction and hematoendothelial specification and define specific growth factors required for step-wise progression of differentiation toward HE and blood cells in hPSC cultures (FIG. 1) differentiated in chemically-defined conditions on ColIV and TenC. During embryonic development, BMP4, Wnt, and TGFβ/Nodal/Activin A signaling have been found to be critical to initiate primitive streak formation and subsequent mesoderm development[27,28]. It has been shown that activation of these signaling pathways is essential to induce the expression of brachyury and KDR (Flk-1, VEGFR2), and initiate mesodermal commitment of mouse and human PSCs[18,19,29-32]. We have found that high concentrations of BMP4 (50 ng/ml) combined with low concentrations of Activin A (15 ng/ml) and a supplement of LiCl (2 mM) consistently induced expression of the mesodermal surface markers APLNR, KDR, and PDGFRalpha after 2 days of culture of single cell suspension of hESCs on ColIV in chemically-defined conditions as we described above. However, these conditions poorly supported cell survival and required the addition of FGF2 and a hypoxic conditions (5% O$_2$, 5% CO$_2$) to improve cell viability and output of mesodermal cells. Day 2 KDR$^+$ mesodermal cells differentiated in these conditions expressed APLNR and PDGFRalpha, i.e. became APLNR$^+$ PDGFRalpha$^+$ cells and displayed MB colony-forming potential similar to APLNR$^+$PDGFRalpha$^+$ mesodermal cells obtained from day 2 hPSCs differentiated in OP9 coculture[11] (FIG. 3). After 2 days of differentiation, we found that only FGF2 and VEGF are required for APLNR$^+$ PDGFRalpha$^+$ mesoderm to acquire HB potential on day 3 of differentiation and advance mesoderm specification toward HVMPs signified by increase in KDR expression and the decrease in PDGFRalpha expression in APLNR$^+$ cells (KDR$^{hi}$APLNR$^+$PDGFRalpha$^{lo/-}$ phenotype) in CD31$^-$ mesodermal cells on day 4 of differentiation. The pattern of development was similar in cells cultured on ColIV and TenC, however the later one produced significantly higher APLNR$^+$PDGFRalpha$^+$ cells, MB and HB colonies (FIG. 3a, 3c).

Day 4 differentiated hESCs lost capability to form HB colonies (FIG. 3c), however these cells were capable to form hematoendothelial clusters when sorted and plated onto OP9 in αMEM supplemented with 10% FBS, SCF, TPO, IL6, and IL3. The hematoendothelial cluster potential was restricted to KDR$^{hi}$APLNR$^+$PDGFRalpha$^{lo/-}$CD31$^-$ HVMPs (FIG. 3d). The KDR$^{lo}$CD31$^-$ cells only formed endothelial clusters with almost no hemogenic activity (FIG. 3d), while KDR– cells fail to grow both, endothelial and blood cells (not shown). This is also consistent with differentiation in OP9 coculture[6]. The percentage of KDR$^{hi}$APLNR$^+$PDG-FRalpha$^{lo/-}$ HVMPs cells was consistently higher in TenC cultures (FIG. 3a).

Because formation of HVMPs in hPSC/OP9 cocultures is closely followed by development of HE and blood progenitors, we supplemented our cultures with SCF, TPO, IL-6, and IL-3 hematopoietic cytokines in addition to VEGF and FGF2 starting from day 4 of differentiation. Although we noticed that the continuous treatment of cultures with FGF2 and VEGF was sufficient for induction of endothelial progenitors and hematopoietic specification, addition of hematopoietic cytokines was essential to increase output of these cells in chemically defined cultures. On day 5 of differentiation in these conditions, the previously identified 3 major subsets of the CD144[+] populations[6] emerged: CD144[+]CD43[-]CD73[+], CD144[+]CD43[-]CD73[-] and CD144[+]CD43/CD235a[+]CD41a[-] (FIG. 4). When these subsets were sorted and plated into endothelial conditions, all of them formed a monolayer of VE-cadherin expressing cells with capacity to uptake AcLDL and form vascular tubes in the tube formation assay, consistent with OP9 coculture (FIG. 4*d*). However, hematopoietic CFC potential was mostly restricted to CD144[+]CD43/CD235a[+]CD41a[-] cells (FIG. 4*c*). Importantly similar to finding with day 5 CD144[+] subsets generated in coculture with OP9, the hematopoietic CFC potential of CD144[+]CD43/CD235a[+]CD41a[-] cells was detected only in serum-free medium in presence of FGF2 in addition to hematopoietic cytokines, indicating that these cells essentially similar to AHP identified in hPSC/OP9 coculture[6]. We previously defined HEP as CD144[+]CD43[-]CD73[-] cells lacking hematopoietic CFC potential, but capable to acquire it after culture on OP9. To determine whether CD144[+]CD43[-]CD73[-] generated in completely defined conditions similar to OP9-induced HEPs, we sorted day 5 CD144[+] subsets and cultured with OP9 as previously described[6]. In these conditions, the HEPs formed both endothelial and hematopoietic cells with large number of HE-clusters, while AHPs formed predominantly hematopoietic cells with few endothelial cells and hematoendothelial clusters. CD144[+]CD43[-]CD73[+] cells formed endothelial clusters only consistent with non-HEP phenotype (FIG. 4*d*). Cultures differentiated on TenC had a larger population of total CD144[+] cells, thereby increasing the population of HEPs, non-HEPs, and AHPs compared to cultures differentiated on ColIV (FIG. 4*a, b*).

Figures 5A, 5B, 5C, 5D:
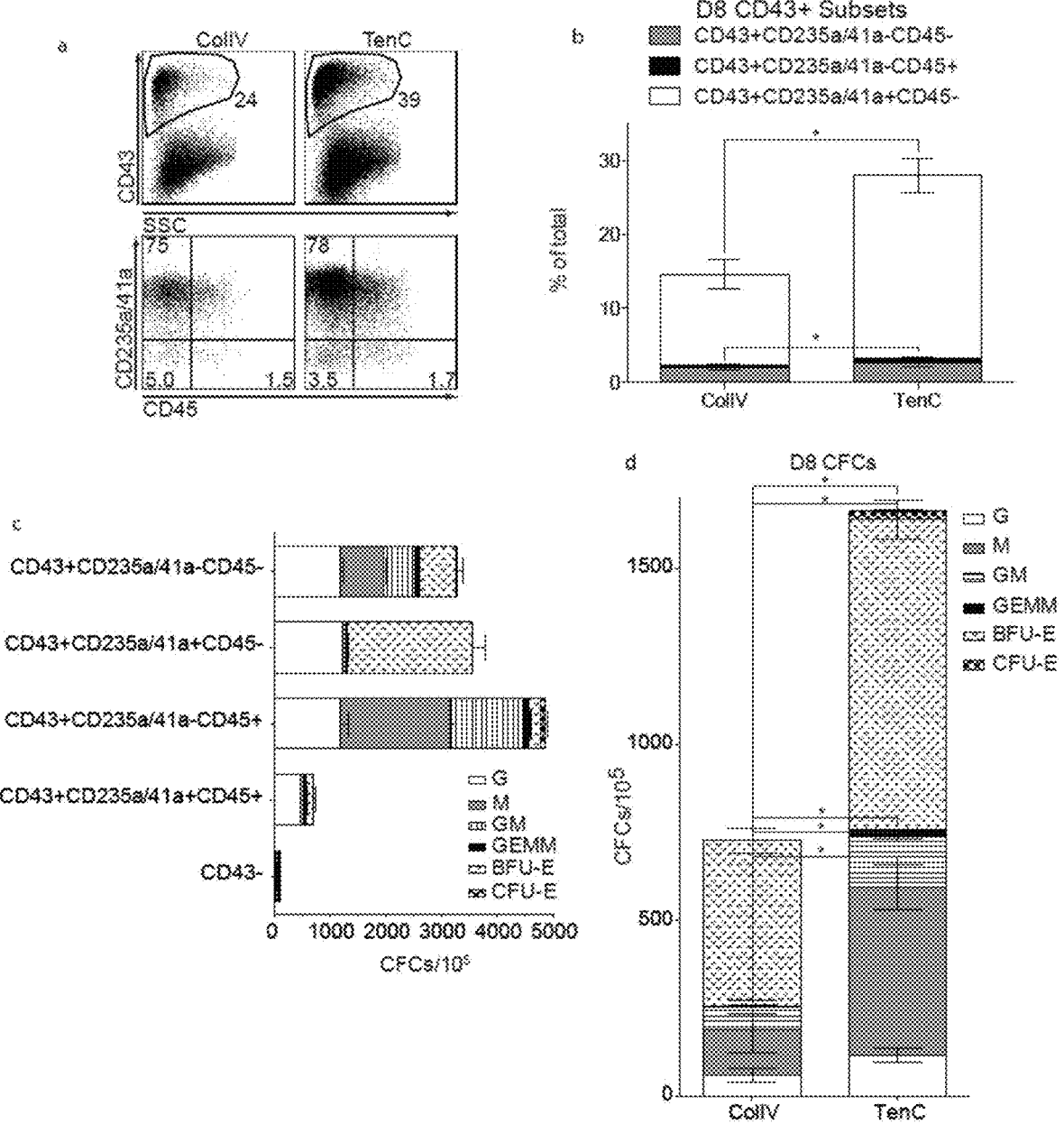
FIGS. 5A-5D Development of hematopoietic progenitors in cultures differentiated on CollV for 8 days in chemically defined conditions. (a) Flow cytometric analysis shows major subsets of CD43+ cells generated in cultures on CollV and TenC. (b) Cultures on TenC produce significantly more CD43+ cells across 3 experiments (*p<0.01). (c) Hematopoietic-CFC potential in serum-containing media is limited to the CD43+ subpopulations. (d) Cultures differentiated on TenC have higher CFC potential than cultures differentiated on ColIV, statistically significant across 3 experiments (*p<0.01).

When numerous floating round hematopoietic cells became visible in cultures on day 6, the hypoxic conditions were not necessary to sustain hematopoietic development. Therefore, from day 6 of differentiation, the cultures were transferred cells to a normoxic incubator (20% $O_2$, 5% $CO_2$). By day 8 of differentiation, cultures showed development of large number of CD43+ hematopoietic cells composed CD235a[+]CD41a[+] cells enriched in erythro-megakaryocytic progenitors and lin[-]CD43[+]CD45[-/+] cells which expressed CD34 (FIG. 5) and lacked of other lineage markers (not shown). Consistent with cells differentiated on OP9, hematopoietic colony forming potential was limited to the CD43[+] subpopulations (FIG. 5*c*). CD43[+] hematopoetic progenitors expanded significantly more on TenC compared to ColIV (FIG. 5*b*). In addition, the GEMNI-CFC potential of cultures on TenC was significantly greater than cultures on ColIV (FIG. 5*d*).

Figure 9:
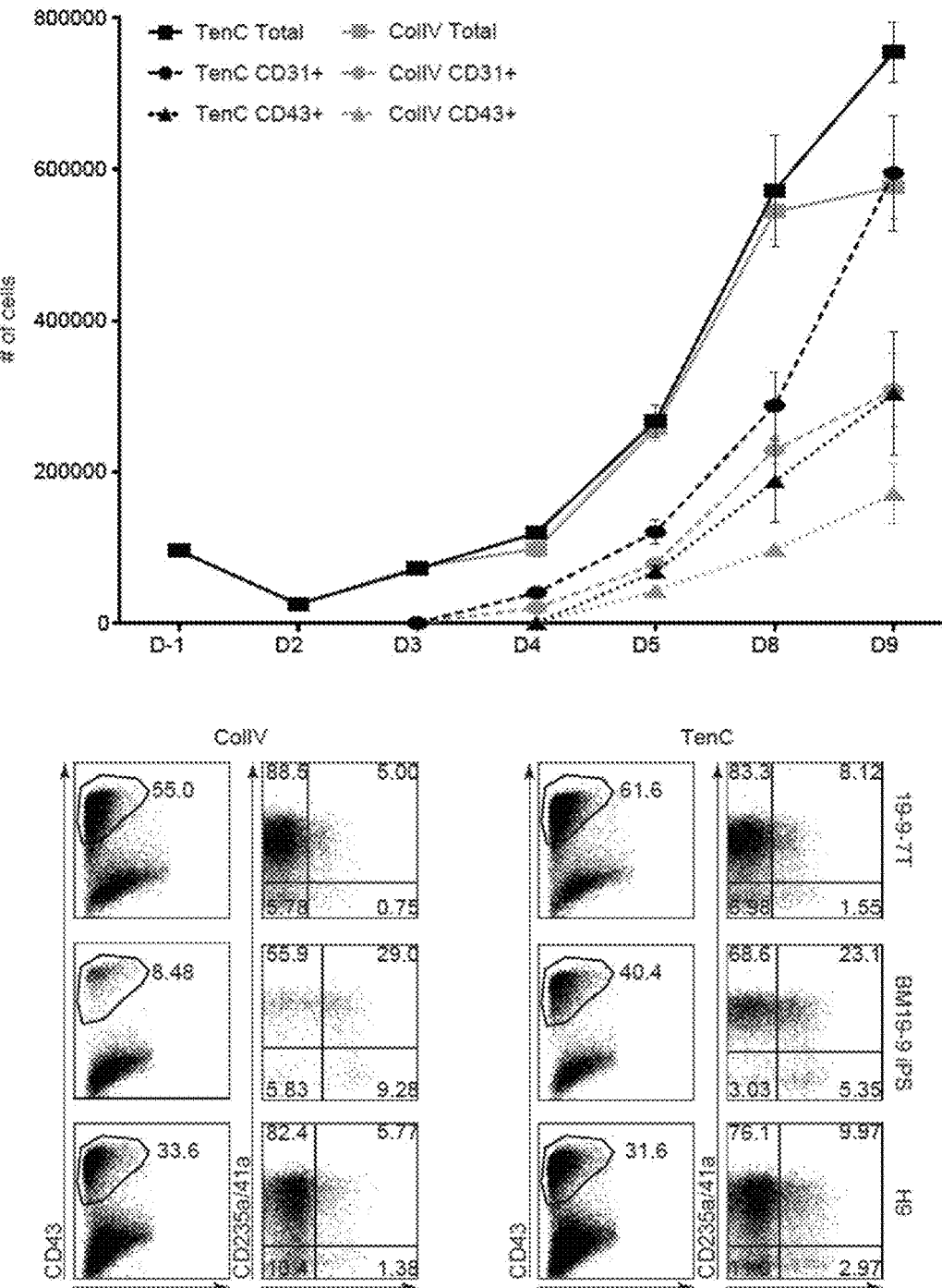
FIG. 9 Hematopoietic differentiation of iPSCs and hESCs in chemically defined conditions. Top panel represents the number of cells generated in cultures starting from day −1 when cells are plated on either TenC or ColIV, up to day 9 of differentiation. The numbers of CD31$^+$ and CD43$^+$ cells were calculated based on total number of cells times the percentage of positive cells based on flow cytometry. The bottom panel displays dot plots of the percentage of CD43$^+$ cells and their subsets of 19-9-7T human fibroblast iPSC line, BM19-9 human bone marrow-derived iPSC line, and H9 human ESC line differentiated for eight days on either ColIV or TenC.

Although the differentiation protocol was initially developed using H1 hESCs, we found that chemically defined conditions described here also supports formation of HE and blood from other hESCs (H9) and hiPSCs generated from fibroblasts or bone marrow mononuclear cells (FIG. 9). Previously, we found that hiPSC obtained through reprogramming of cord blood mononuclear cells (CB hiPSCs) differentiate less efficiently into the blood cells on OP9 feeders compared to fibroblast-derived (FB) hiPSCs[33]. These findings have been reproduced when we differentiated CB and FB iPSCs on ColIV. However, differentiation on TenC restored hematopoietic differentiation potential of CB hiPSCs to the level seen with hESCs and FB hiPSCs (FIG. 9), thereby confirming that TenC is superior over ColIV in promoting hematopoietic differentiation from hPSCs.

Figures 6A, 6B, 6C:
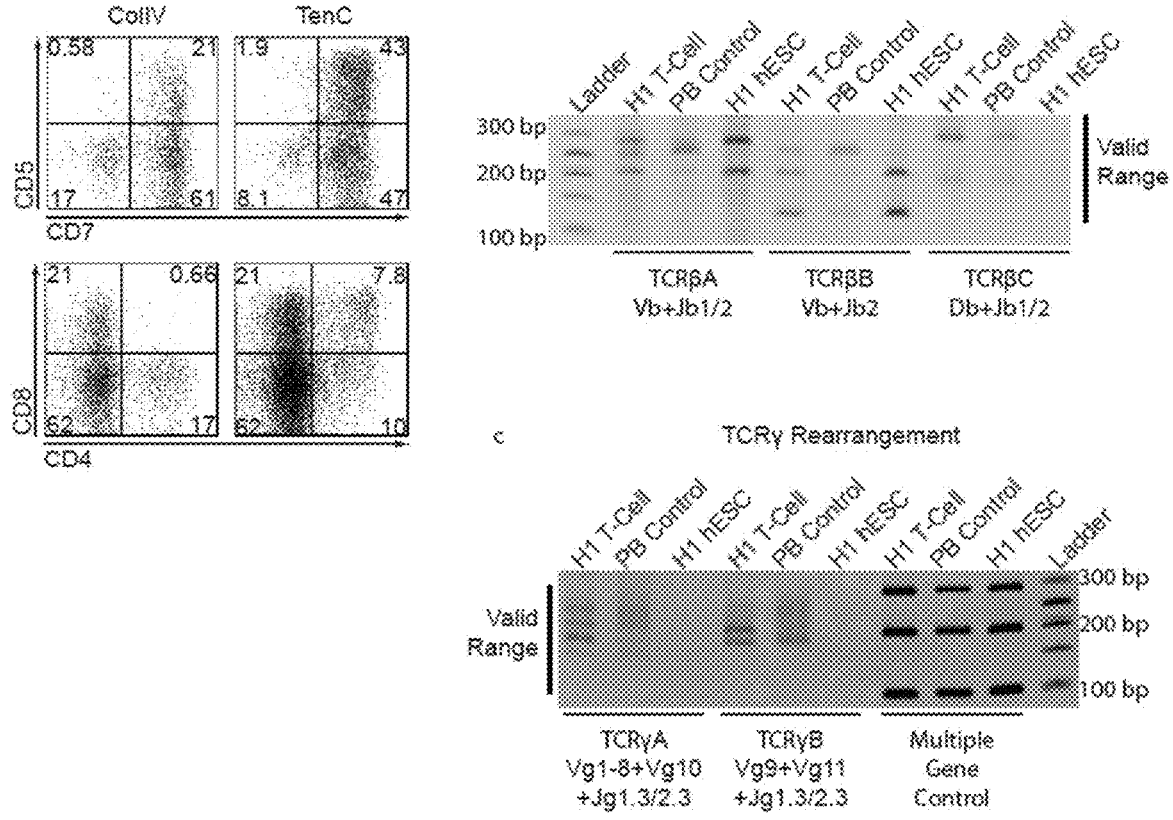
FIGS. 6A-6C T cell potential of CD43+ cells collected from H1 hESCs differentiated for 9 days in chemically defined conditions on ColIV and TenC. (a) Flow cytometric analysis of cells collected from ColIV and TenC conditions after culture on OP9DLL4 for 3 weeks. (b and c) Analysis for T cell receptor rearrangement by genomic PCR. H1 T-Cell is the T-cells derived from differentiating H1; PB control is Peripheral Blood positive control; H1 hESC is undifferentiated H1 hESCs.

Example 4 Tenascin C Uniquely Supports Specification of T Lymphoid Progenitors from hPSCs To find out whether our culture system supports establishment of definitive hematopoietic program from hPSCs, we analyzed T cell potential of blood cells generated in our system as indicator of definitive hematopoiesis[7]. When we collected CD43[+] floating cells from day 9 differentiated cultures, and replated them onto OP9 cells expressing DLL-4 in α-MEM with 20% FBS, Flt3L, IL-7, and SCF, CD7[+]CD5[+] lymphoid progenitors began to emerge by week 2 of secondary coculture. By week 3, CD4[+]CD8[+] double positive T-cells arose (FIG. 6*a*).

Interestingly, CD43[+] cells generated on both ColIV and TenC matrices had a capacity to generate CD5[+]CD7[+] lymphoid progenitors. However, progression toward CD4[+]CD8[+] T lymphoid cells was observed only from CD43[+] cells generated on TenC but not on ColIV. To confirm T cell development, we analyzed genomic DNA from these cultures for the presence of TCR rearrangements. This analysis demonstrated the presence of multiple PCR products of random V-J and D-J rearrangements at the γ-locus and multiple V-J and rearrangements at the γ-locus indicative of polyclonal T lineage repertoire (FIGS. 6*b* and 6*c*). Overall, these findings signify that extracellular matrix Tenascin C is essential for supporting definitive hematopoiesis in completely chemically defined conditions.

Figure 7:
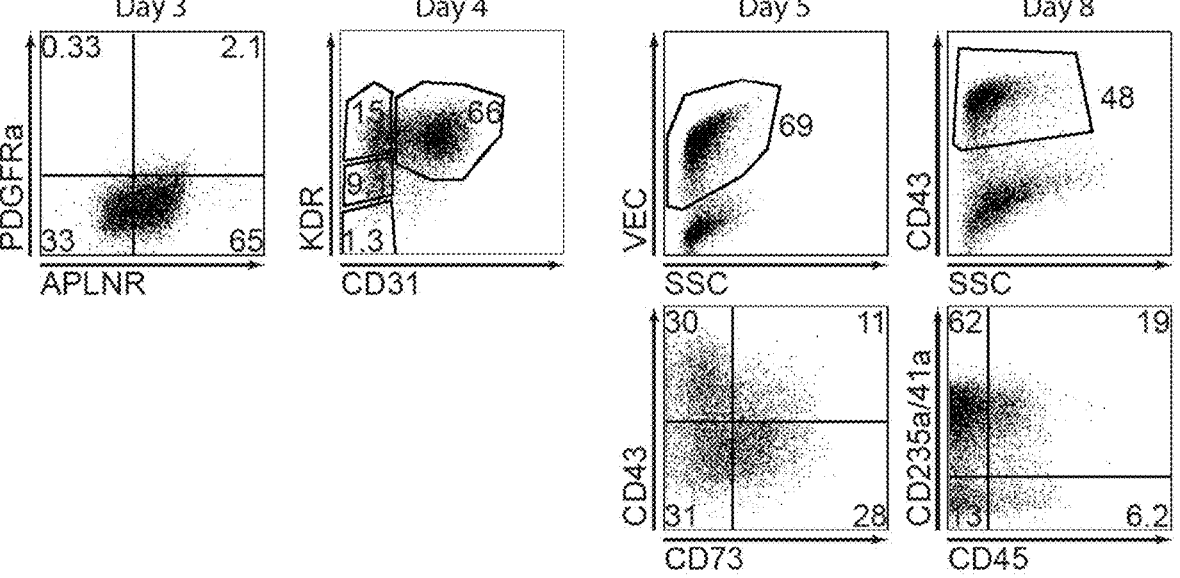
FIG. 7 The effect TGFβ inhibitor on hematopoietic development from H1 hESCs in chemically defined conditions. Representative dot plots collected from flow cytometry of day 3, 4, 5, and 8 of differentiation after adding the TGFβ inhibitor, SB-431542 from day 2 to day 4 only. On day 3, SB-431542 decreases PDGFRalpha expression, but increases endothelial progenitors by days 4 and 5. By day 8, there is a significant increase in CD43+ hematopoietic progenitors.

Example 5 Inhibition of TGF-β Promotes Hematoendothelial Specification in Chemically Defined Conditions Recent studies have shown that adding TGF-β inhibitors after mesoderm specification but before endothelial development increases definitive hematopoietic differentiation. We found that when 10 μM of SB-431542, a potent but non-specific TGFβ inhibitor, is added from day 2 to day 4, it significantly decreases the development of PDGFRalpha-positive mesoderm cells by day 3, and increases CD31[+] differentiation by day 4. After day 4, SB-431542 is no longer added, but the effect of the 2 day treatment continues to increase CD43[+] population by day 9 (FIG. 7).

During the last decade significant progress has been made in hematopoietic differentiation from hPSCs. Multiple protocols for hematopoietic differentiation have been developed and made it possible routinely produce blood cells for experimentation. However, generation of blood cells with long-term reconstitution potential, HSCs, from hPSCs remains significant challenge. In the embryo, hematopoietic cells and HSCs arise from specific subset of endothelium (HE)[1-5], thus the ability to interrogate signaling pathways leading to HE specification and transition into the blood cells in completely chemically defined environment is essential for identification of factors required for HSC specification and eventually development of conditions for de novo HSC generation. Although original protocols for hematopoietic differentiation have employed xenogenic, feeder and/or serum, several serum- and feeder-free systems for hematopoietic differentiation have been described recently[18,34,35] However, these protocols still requires serum components (albumin), and it remains unclear whether these protocols reproduce distinct waves of hematopoiesis, including generation of HE with definitive lymphomyeloid potential, observed in the original differentiation systems. More recently Kennedy et al,[7] have developed feeder- and stroma-free conditions for EB-based hematopoietic differentiation of hPSCs and showed that these conditions reproduced primitive and definitive waves of hematopoiesis and generate HE with T lymphoid potential. However, this protocol uses hPSCs growing on MEFs for EB-based hematopoietic differentiation in proprietary medium with non-disclosed chemical and human protein content. Here we developed for the first time protocol that enable efficient production of blood cells in completely chemically defined conditions free of serum and xenogeneic proteins from a single cell suspension of hPSCs maintained in chemically defined E8 medium[12]. This protocol eliminates variability associated with animal- or human-sourced albumins, xenogenic matrix, clump sizes and asynchronous differentiation observed in EB system and reproduces typical waves of hematopoiesis, including formation of HE and definitive hematopoietic progenitors, observed in hPSCs differentiated on OP9. Importantly, based on molecular profiling of OP9 and stromal cell lines with different hematopoiesis-inducing activity, we found that TenC matrix protein uniquely expressed in OP9 with robust hemato-inducing potential, strongly promotes hematoendothelial and T lymphoid development from hPSCs. TenC is disulfide-linked hexameric glycoprotein that is mainly expressed during embryonic development. Although TenC mostly disappear in adult organism, its expression upregulated during wound repair, neovascularization and neoplasia.[36] Interestingly TenC is found in adult bone marrow where it expressed predominantly in endosteal region[37,38] and upregulated following myeloablation[25]. TenC supports proliferation of bone marrow hematopoietic cells[39] and erythropoiesis[40]. TenC-deficient mice had lower bone marrow CFC potential[24], failed to reconstitute hematopoiesis after bone marrow ablation and showed reduced ability to support engraftment of wild type HSCs[25]. High level of TenC expression was also detected in human and chicken aorta-gonad-mesonephros (AGM) region[23,41], the site where the first HSC emerge, and hematopoietic sites in the human fetal liver[42]. Because TenC expression is highly enriched in subaortic mesenchyme right underneath of hematopoietic clusters, it was suggested that TenC plays pivotal role in HSC development during embryogenesis[23]. TenC is also involved in regulation of angiogenesis and cardiac endothelial progenitors[43]. Our studies demonstrated the superior properties of TenC in promoting hematopoiesis from hPSCs. The positive effect of TenC was obvious at all stages of differentiation and included the enhancement of hemogenic mesoderm, HE and CD43[+] hematopoietic progenitors production. Importantly, TenC was able to support development of definitive hematopoietic cells with T lymphoid potential, while we were not able to obtain such cells in cultures on CollV. TenC molecule is composed of an amino-terminal oligomerization region followed by heptad repeats, EGF-like and fibronectin type III repeats and fibrinogen globe[36]. The function of these domains is poorly understood. It is believed that effect and interaction of TenC with cells requires the integrate action of multiple domains[44], although several unique mitogenic domains capable of inducing a proliferation of hematopoietic cells were identified within this molecule[39]. Several signaling mechanisms implicated in cell interaction with TenC have been identified, including suppression of fibronectin-activated focal adhesion kinase- and Rho-mediated signaling and stimulation of Wnt signaling (reviewed in[45]). Further studies aimed to identify mechanism of TenC action on hPSCs and their hematopoietic derivatives would be of value to understand the role of this matrix protein in hematopoietic development.

In summary, the findings provided here identified TenC matrix proteins and completely chemically defined conditions free of serum/serum components and animal proteins capable of supporting the scalable production of HE and definitive blood cells from hPSCs. This differentiation system allows precise interrogation of signaling molecules implicated in hematopoietic differentiation and provide platform for production of cGMP grade of blood cells for clinical application.

REFERENCES

1 Boisset, J. C. et al. In vivo imaging of haematopoietic cells emerging from the mouse aortic endothelium. *Nature* 464, 116-120, doi:nature08764 [pii] 10.1038/nature08764 (2010).

2 Kissa, K. & Herbomel, P. Blood stem cells emerge from aortic endothelium by a novel type of cell transition. *Nature* 464, 112-115, doi:nature08761 [pii] 10.1038/nature08761 (2010).

3 Bertrand, J. Y. et al. Haematopoietic stem cells derive directly from aortic endothelium during development. *Nature* 464, 108-111, doi:nature08738 [pii] 10.1038/nature08738 (2010).

4 Zovein, A. C. et al. Fate tracing reveals the endothelial origin of hematopoietic stem cells. *Cell Stem Cell* 3, 625-636. (2008).

5 Jaffredo, T., Gautier, R., Brajeul, V. & Dieterlen-Lievre, F. Tracing the progeny of the aortic hemangioblast in the avian embryo. *Dev Biol* 224, 204-214, doi:10.1006/dbio.2000.9799 S0012-1606(00)99799-9 [pii] (2000).

6 Choi, K. D. et al. Identification of the hemogenic endothelial progenitor and its direct precursor in human pluripotent stem cell differentiation cultures. *Cell Rep* 2, 553-567, doi:10.1016/j.celrep.2012.08.002 (2012).

7 Kennedy, M. et al. T lymphocyte potential marks the emergence of definitive hematopoietic progenitors in human pluripotent stem cell differentiation cultures. *Cell Rep* 2, 1722-1735, doi:10.1016/j.celrep.2012.11.003 (2012).

8 Rafii, S. et al. Human ESC-derived hemogenic endothelial cells undergo distinct waves of endothelial to hematopoietic transition. *Blood*, doi:10.1182/blood-2012-07-444208 (2012).

9 Vodyanik, M. A., Bork, J. A., Thomson, J. A. & Slukvin, II. Human embryonic stem cell-derived CD34+ cells: efficient production in the coculture with OP9 stromal cells and analysis of lymphohematopoietic potential. *Blood* 105, 617-626. (2005).

10 Vodyanik, M. A., Thomson, J. A. & Slukvin, II. Leukosialin (CD43) defines hematopoietic progenitors in human embryonic stem cell differentiation cultures. *Blood* 108, 2095-2105 (2006).

11 Vodyanik, M. A. et al. A mesoderm-derived precursor for mesenchymal stem and endothelial cells. *Cell Stem Cell* 7, 718-729, doi:S1934-5909(10)00633-8 [pii] 10.1016/j.stem.2010.11.011 (2010).

12 Chen, G. et al. Chemically defined conditions for human iPSC derivation and culture. *Nat Methods* 8, 424-429, doi:nmeth.1593 [pii] 10.1038/nmeth.1593 (2011).

13 Vodyanik, M. A. & Slukvin, II. Hematoendothelial differentiation of human embryonic stem cells. *Curr Protoc Cell Biol* Chapter, Unit 23.26. (2007).

14 Choi, K. D., Vodyanik, M. & Slukvin, II. Hematopoietic differentiation and production of mature myeloid cells from human pluripotent stem cells. *Nat Protoc* 6, 296-313, doi:nprot.2010.184 [pii] 10.1038/nprot.2010.184 (2011).

15 Ng, E. S., Davis, R. P., Azzola, L., Stanley, E. G. & Elefanty, A. G. Forced aggregation of defined numbers of human embryonic stem cells into embryoid bodies fosters robust, reproducible hematopoietic differentiation. *Blood* 106, 1601-1603. Epub 2005 May 1624. (2005).

16 Wang, L. et al. Endothelial and hematopoietic cell fate of human embryonic stem cells originates from primitive endothelium with hemangioblastic properties. *Immunity* 21, 31-41 (2004).

17 Chen, G. et al. Chemically defined conditions for human iPSC derivation and culture. *Nature methods* 8, 424-429, doi:10.1038/nmeth.1593 (2011).

18 Salvagiotto, G. et al. A defined, feeder-free, serum-free system to generate in vitro hematopoietic progenitors and differentiated blood cells from hESCs and hiPSCs. *PLoS One* 6, e17829, doi:10.1371/journal.pone.0017829 (2011).

19 Pick, M., Azzola, L., Mossman, A., Stanley, E. G. & Elefanty, A. G. Differentiation of human embryonic stem cells in serum-free medium reveals distinct roles for bone morphogenetic protein 4, vascular endothelial growth factor, stem cell factor, and fibroblast growth factor 2 in hematopoiesis. *Stem Cells* 25, 2206-2214. Epub 27 Jun. 2207. (2007).

20 Himburg, H. A. et al. Pleiotrophin regulates the expansion and regeneration of hematopoietic stem cells. *Nature medicine* 16, 475-482, doi:10.1038/nm.2119 (2010).

21 Kazanskaya, O. et al. The Wnt signaling regulator R-spondin 3 promotes angioblast and vascular development. *Development* 135, 3655-3664, doi:10.1242/dev.027284 (2008).

22 Siewe, B. T. et al. In vitro requirement for periostin in B lymphopoiesis. *Blood* 117, 3770-3779, doi:10.1182/blood-2010-08-301119 (2011).

23 Marshall, C. J. et al. Detailed characterization of the human aorta-gonad-mesonephros region reveals morphological polarity resembling a hematopoietic stromal layer. *Dev Dyn* 215, 139-147, doi:10.1002/(SICI)1097-0177(199906)215:2<139::AID-DVDY6>3.0.00; 2-# (1999).

24 Ohta, M., Sakai, T., Saga, Y., Aizawa, S. & Saito, M. Suppression of hematopoietic activity in tenascin-C-deficient mice. *Blood* 91, 4074-4083 (1998).

25 Nakamura-Ishizu, A. et al. Extracellular matrix protein tenascin-C is required in the bone marrow microenvironment primed for hematopoietic regeneration. *Blood* 119, 5429-5437, doi:10.1182/blood-2011-11-393645 (2012).

26 Slukvin, II. Deciphering the hierarchy of angiohematopoietic progenitors from human pluripotent stem cells. *Cell Cycle* 12, 720-727, doi:10.4161/cc.23823 (2013).

27 Gadue, P., Huber, T. L., Nostro, M. C., Kattman, S. & Keller, G. M. Germ layer induction from embryonic stem cells. *Experimental hematology* 33, 955-964, doi: 10.1016/j.exphem.2005.06.009 (2005).

28 Keller, G. Embryonic stem cell differentiation: emergence of a new era in biology and medicine. *Genes & development* 19, 1129-1155, doi:10.1101/gad.1303605 (2005).

29 Pearson, S., Sroczynska, P., Lacaud, G. & Kouskoff, V. The stepwise specification of embryonic stem cells to hematopoietic fate is driven by sequential exposure to Bmp4, activin A, bFGF and VEGF. *Development* 135, 1525-1535, doi:10.1242/dev.011767 (2008).

30 Nostro, M. C., Cheng, X., Keller, G. M. & Gadue, P. Wnt, activin, and BMP signaling regulate distinct stages in the developmental pathway from embryonic stem cells to blood. *Cell Stem Cell* 2, 60-71, doi:S1934-5909(07)00228-7 [pii] 10.1016/j.stem.2007.10.011 (2008).

31 Cerdan, C. et al. Activin A promotes hematopoietic fated mesoderm development through upregulation of brachyury in human embryonic stem cells. *Stem cells and development* 21, 2866-2877, doi:10.1089/scd.2012.0053 (2012).

32 Kennedy, M., D'Souza, S. L., Lynch-Kattman, M., Schwantz, S. & Keller, G. Development of the hemangioblast defines the onset of hematopoiesis in human ES cell differentiation cultures. *Blood* 109, 2679-2687. (2007).

33 Hu, K. et al. Efficient generation of transgene-free induced pluripotent stem cells from normal and neoplastic bone marrow and cord blood mononuclear cells. *Blood* 117, e109-119, doi:blood-2010-07-298331 [pii] 10.1182/blood-2010-07-298331 (2011).

34 Smith, B. W. et al. The aryl hydrocarbon receptor directs hematopoietic progenitor cell expansion and differentiation. *Blood* 122, 376-385, doi:10.1182/blood-2012-11-466722 (2013).

35 Wang, C. et al. TGFbeta inhibition enhances the generation of hematopoietic progenitors from human ES cell-derived hemogenic endothelial cells using a stepwise strategy. *Cell research* 22, 194-207, doi:10.1038/cr.2011.138 (2012).

36 Hsia, H. C. & Schwarzbauer, J. E. Meet the tenascins: multifunctional and mysterious. *The Journal of biological chemistry* 280, 26641-26644, doi:10.1074/jbc.R500005200 (2005).

37 Soini, Y., Kamel, D., Apaja-Sarkkinen, M., Virtanen, I. & Lehto, V. P. Tenascin immunoreactivity in normal and pathological bone marrow. *J Clin Pathol* 46, 218-221 (1993).

38 Klein, G., Beck, S. & Muller, C. A. Tenascin is a cytoadhesive extracellular matrix component of the human hematopoietic microenvironment. *J Cell Biol* 123, 1027-1035 (1993).

39 Seiffert, M. et al. Mitogenic and adhesive effects of tenascin-C on human hematopoietic cells are mediated by various functional domains. *Matrix Biol* 17, 47-63 (1998).

40 Seki, M. et al. Identification of tenascin-C as a key molecule determining stromal cell-dependent erythropoiesis. *Experimental hematology* 34, 519-527, doi: 10.1016/j.exphem.2006.01.001 (2006).

41 Anstrom, K. K. & Tucker, R. P. Tenascin-C lines the migratory pathways of avian primordial germ cells and hematopoietic progenitor cells. *Dev Dyn* 206, 437-446, doi:10.1002/(SICI)1097-0177(199608)206:4<437::AID-AJA9>3.0.00; 24 (1996).

42 Papadopoulos, N. et al. Induction of hepatic hematopoiesis with tenascin-C expression during the second trimester of development. *Eur J Obstet Gynecol Reprod Biol* 113, 56-60, doi:10.1016/j.ejogrb.2003.05.006 (2004).

43 Ballard, V. L. et al. Vascular tenascin-C regulates cardiac endothelial phenotype and neovascularization. *FASEB journal: official publication of the Federation of American Societies for Experimental Biology* 20, 717-719, doi:10.1096/fj.05-5131fje (2006).

44 Fischer, D., Brown-Ludi, M., Schulthess, T. & Chiquet-Ehrismann, R. Concerted action of tenascin-C domains in cell adhesion, anti-adhesion and promotion of neurite outgrowth. *J Cell Sci* 110 (Pt 13), 1513-1522 (1997).

45 Orend, G. Potential oncogenic action of tenascin-C in tumorigenesis. *Int J Biochem Cell Biol* 37, 1066-1083, doi:10.1016/j.biocel.2004.12.002 (2005).

46 Vodyanik, M. A. & Slukvin, II. Hematoendothelial differentiation of human embryonic stem cells. *Current protocols in cell biology/editorial board*, Juan S. Bonifacino . . . [et al.] Chapter 23, Unit 23 26, doi:10.1002/0471143030.cb2306s36 (2007).

47 Irizarry, R. A. et al. Exploration, normalization, and summaries of high density oligonucleotide array probe level data. *Biostatistics* 4, 249-264, doi:10.1093/biostatistics/4.2.249 [doi] 4/2/249 [pii] (2003).

We claim:

1. A xenogen-free, albumin-free culture system capable of differentiating human pluripotent stem cells into mesoderm, endothelial and hematopoietic progenitor cells comprising:
   a) a solid substrate comprising a layer of Tenascin C or collagen; and
   b) xenogen-free and albumin-free culture medium comprising:
      about 50 to about 250 ng/ml BMP4;
      about 10 to about 15 ng/ml Activin A;
      about 10 to about 50 ng/ml FGF2; and
      about 1 to about 2 mM LiCl,
   wherein the culture system, when seeded with human pluripotent stem cells, produces $^{EMH}$lin$^-$KDR$^+$APLNR$^+$PDGFRalpha$^+$primitive mesoderm cells.

2. The xenogen-free, albumin-free culture system of claim 1, wherein the medium further comprises a base medium, L-ascorbic acid 2-phopshate Mg$^{2+}$salt monothioglycerol, sodium selenite, polyvinyl alcohol, non-essential amino acids (NEAA), chemically defined lipid concentrate, holo-transferrin, and insulin.

3. The xenogen-free, albumin-free culture system of claim 2, wherein the medium comprises 64 mg/L L-ascorbic acid 2-Phosphate Mg$^{2+}$salt, 40 μl/L monothioglycerol, 8.4 μg/L additional sodium selenite, 10 mg/L polyvinyl alcohol, 1× non-essential amino acids, 0.1×chemically-defined lipid concentrate, 10.6 mg/L holo-transferrin, and 20 mg/L insulin.

4. The xenogen-free culture system of claim 1, wherein the medium of step b further comprises: about 50 to about 100 ng/ml stem cell factor (SCF), about 50 to about 100 ng/ml thrombopoietin (TPO), about 50 to about 100 ng/ml IL-6, and about 5 to about 15 ng/ml IL-3.

5. The xenogen-free, albumin-free culture system of claim 1, wherein the human pluripotent stem cells can be seeded at a concentration of about 0.25 μg/cm$^2$ to about 1 μg/cm$^2$.

6. The xenogen-free, albumin-free culture system of claim 1, wherein the solid substrate comprises a layer of Tenascin C.

7. The xenogen-free, albumin-free culture system of claim 6, wherein the layer of Tenascin C is at a concentration of about 0.25 μg/cm$^2$ to about 1 μg/cm$^2$.

8. The xenogen-free culture system of claim 1, wherein the solid substrate of (a) further comprises human pluripotent stem cells seeded thereupon.

9. The xenogen-free, albumin-free culture system of claim 1, wherein the solid substrate comprises a layer of collagen.

* * * * *